(12) United States Patent
Bailey et al.

(10) Patent No.: US 12,285,636 B2
(45) Date of Patent: Apr. 29, 2025

(54) NON-PLANAR HOLOGRAPHIC BEAM SHAPING LENSES FOR ACOUSTICS

(71) Applicant: University of Washington, Seattle, WA (US)

(72) Inventors: Michael R. Bailey, Seattle, WA (US); Mohamed Abdalla Ghanem, Seattle, WA (US); Adam D. Maxwell, Seattle, WA (US)

(73) Assignee: The University of Washington, Seattle, WA (US)

( * ) Notice: Subject to any disclaimer, the term of this patent is extended or adjusted under 35 U.S.C. 154(b) by 70 days.

(21) Appl. No.: 17/881,026

(22) Filed: Aug. 4, 2022

(65) Prior Publication Data
US 2023/0038081 A1 Feb. 9, 2023

Related U.S. Application Data

(60) Provisional application No. 63/230,003, filed on Aug. 5, 2021.

(51) Int. Cl.
*A61N 7/00* (2006.01)
*B29D 11/00* (2006.01)
*G02B 5/32* (2006.01)

(52) U.S. Cl.
CPC .......... *A61N 7/00* (2013.01); *B29D 11/00009* (2013.01); *G02B 5/32* (2013.01); *A61N 2007/006* (2013.01)

(58) Field of Classification Search
CPC ............... A61N 2007/006; A61N 7/00; B29D 11/00009; G02B 5/32
See application file for complete search history.

(56) References Cited

U.S. PATENT DOCUMENTS

| 4,475,921 A | 10/1984 | Barmatz |
| 5,902,489 A | 5/1999 | Yasuda et al. |

(Continued)

FOREIGN PATENT DOCUMENTS

| CA | 2864665 A1 | 8/2013 |
| CN | 101955595 A | 1/2011 |

(Continued)

OTHER PUBLICATIONS

Karzova, "Shock formation and nonlinear saturation effects in the ultrasound field of a diagnostic curvilinear probe", Acoustical Society of America, 2017 (Year: 2017).*

(Continued)

*Primary Examiner* — Joel Lamprecht
*Assistant Examiner* — Brooke Lyn Klein
(74) *Attorney, Agent, or Firm* — Christensen O'Connor Johnson Kindness PLLC

(57) ABSTRACT

Non-planar holographic beam shaping lenses for acoustics are disclosed herein. In one embodiment, an ultrasonic therapy system that is configured to apply ultrasound to a target in a body includes: an ultrasonic transducer configured to generate the ultrasound; and a customizable holographic lens configured to focus the ultrasound onto a focal area of a target that is an object or a portion of the object in the body. The customizable holographic lens is designed and produced based on the target. Furthermore, the customizable holographic lens is curved to mate with a front surface of the ultrasonic transducer.

8 Claims, 15 Drawing Sheets

(56) References Cited

U.S. PATENT DOCUMENTS

| | | | |
|---|---|---|---|
| 7,837,623 | B2 | 11/2010 | Aubry |
| 8,509,928 | B2 | 8/2013 | Abate |
| 9,901,753 | B2 | 2/2018 | Cain |
| 10,251,657 | B1 | 4/2019 | Maxwell |
| 2008/0194965 | A1 | 8/2008 | Sliwa et al. |
| 2012/0029393 | A1 | 2/2012 | Lee |
| 2013/0289593 | A1 | 10/2013 | Hall |
| 2013/0301383 | A1 | 11/2013 | Sapozhnikov |
| 2014/0058292 | A1 | 2/2014 | Alford et al. |
| 2016/0114193 | A1 | 4/2016 | Prus |
| 2016/0185056 | A1 | 6/2016 | Beachum et al. |
| 2016/0317842 | A1 | 11/2016 | Sliwa |
| 2017/0094265 | A1 | 3/2017 | Mullins |
| 2017/0226473 | A1 | 8/2017 | Chen et al. |
| 2017/0245874 | A1 | 8/2017 | Bailey |
| 2017/0296216 | A1 | 10/2017 | Du |
| 2017/0311804 | A1 | 11/2017 | Herring |
| 2018/0070967 | A1 | 3/2018 | Aziz |
| 2018/0110497 | A1 | 4/2018 | Beacham et al. |
| 2018/0192990 | A1 | 7/2018 | Tanter |
| 2018/0341221 | A1* | 11/2018 | Melde ............ A61N 7/02 |
| 2020/0078608 | A1 | 3/2020 | Maxwell |
| 2020/0384463 | A1 | 12/2020 | Davis et al. |
| 2021/0008394 | A1 | 1/2021 | Cain |
| 2021/0101178 | A1 | 4/2021 | Kim |
| 2021/0187330 | A1 | 6/2021 | Bailey |
| 2021/0260578 | A1 | 8/2021 | Shirwaiker et al. |
| 2021/0362145 | A1 | 11/2021 | Kim et al. |
| 2021/0396712 | A1 | 12/2021 | Jimenez Gonzalez |
| 2022/0082690 | A1 | 3/2022 | Lee |
| 2022/0096873 | A1 | 3/2022 | Peyman |
| 2022/0328032 | A1* | 10/2022 | Kim ............ G01N 29/221 |

FOREIGN PATENT DOCUMENTS

| | | | |
|---|---|---|---|
| CN | 106659463 | | 5/2017 |
| CN | 110314715 | A | 10/2019 |
| CN | 111254076 | A | 6/2020 |
| CN | 111326135 | | 6/2020 |
| CN | 213098574 | U | 5/2021 |
| CN | 112946087 | | 6/2021 |
| CN | 112951196 | | 6/2021 |
| CN | 113018514 | A | 6/2021 |
| CN | 113061279 | A | 7/2021 |
| CN | 213722633 | | 7/2021 |
| CN | 113215101 | A | 8/2021 |
| CN | 113604463 | A | 11/2021 |
| CN | 113643683 | | 11/2021 |
| CN | 113826229 | A | 12/2021 |
| CN | 113941030 | A | 1/2022 |
| CR | 20210549 | A | 11/2021 |
| EP | 0134346 | A1 * | 3/1985 ............ G10K 11/32 |
| EP | 3985096 | A1 | 4/2022 |
| JP | 2014198197 | | 10/2014 |
| JP | 2022017543 | | 1/2022 |
| KR | 101261298 | | 5/2013 |
| KR | 20170005526 | | 1/2017 |
| WO | 2006055470 | | 5/2006 |
| WO | 2017097417 | | 6/2017 |
| WO | 2019236409 | | 12/2019 |
| WO | 2021035679 | A1 | 3/2021 |
| WO | 2022032203 | A1 | 2/2022 |
| WO | 2022052179 | | 3/2022 |
| WO | 2022083432 | | 4/2022 |

OTHER PUBLICATIONS

Oleg A. Sapozhnikov, "Acoustic Holography as a metrological tool for characterizing medical ultrasound sources and fields", 2015 ( Year: 2015).*
Ali, C., et al., "Tunable Control and Functional Switch of Transmitted Acoustic Waves by an Arch-Shaped Metasurface," Chinese Journal of Theoretical and Applied Mechanics, 2021, 53(3): 789-801, 2021.
Al-Jumaily, A.M. and A. Meshkinzar, "On the Development of Focused Ultrasound Liquid Atomizers," Advances in Acoustics and Vibration, vol. 2017, pp. 1-10, 2017.
Bailey, M.R., et al., "Progress in Lithotripsy Research," Acoustics Today 2(2):18-29, 2006.
Bakhtiari-Nejad, M., "Multi-focal transmission acoustic phase holograms in contactless ultrasonic power transfer systems," Sensors and Actuators A: Physical, vol. 340, 2022, 113551.
Bigelow, T.A., "Experimental Evaluation of Nonlinear Indices for Ultrasound Transducer Characterizations" master's thesis, Colorado State University, 1998, pp. 99-103, Appendix B: The KLM Model.
Blitz, B.F., et al., "Applicability of Iceland Spar as a Stone Model Standard for Lithotripsy Devices," Journal of Endourology 9(6):449-452, 1995.
Bohris, C., "Quality of Coupling in ESWL Significantly Affects the Disintegration Capacity—How to Achieve Good Coupling With Ultra-Sound Gel," in ed. C. Koehrmann et al., 1st ed., "Therapy Energy Applications in Urology II: Standards Recent Developments," Chap. 2.4, pp. 61-64, 2010.
Chan, W. et al., "Laser-generated focused ultrasound for arbitrary waveforms," Applied Physics Letters 109 (17):174102, 2016.
Chaussy, C., et al., "Extracorporeally Induced Destruction of Kidney Stones by Shock Waves," The Lancet, vol. 316, No. 8207, pp. 1265-1268, 1980.
Chen, L., et al., "High Intensity Focused Ultrasound Ablation for Patients with Inoperable Liver Cancer," Hepato-Gastroenterology 62(137):140-143, 2015.
Chu, B.T.C., "Design of a defocused transducer for targeted cancer drug delivery by ultrasound-mediated hyperthermia, PHD thesis, University of Oxford," 2018, 215 pages.
Cleveland, R., and J. McAteer, "The Physics of Shock Wave Lithotripsy," Smith's Textbook of Endourology, published by B. C. Decker Inc., Hamilton, Ontario, Canada, vol. 1, Chap. 38, pp. 317-331, 2007.
Crum, L.A., "Cavitation Microjets as a Contributory Mechanism for Renal Calculi Disintegration in ESWL," The Journal of Urology 140(6):1587-1590, 1988.
Crum, L.A., and J. B. Fowlkes, "Acoustic cavitation generated by microsecond pulses of ultrasound," Nature, vol. 319, No. 6048, pp. 52-54, 1986.
Delius, M., et al., "A mechanism of gallstone destruction by extracorporeal shock waves.," Naturwissenschaften 75(4):200-201, 1988.
Duryea, A.P., et al., "In Vitro Comminution of Model Renal Calculi Using Histotripsy," IEEE Transactions on Ultrasonics Ferroelectrics and Frequency Control 58(5):971-980, 2011.
Eisenmenger, W., "The mechanisms of stone fragmentation in ESWL.," Ultrasound Medical Biology 27(5):683-693, 2001.
Eisenmenger, W. et al., "The first clinical results of 'wide-focus and low-pressure' ESWL," Ultrasound Medical Biology 28(6):769-774, 2002.
Esch, E., et al., "A simple method for fabricating artificial kidney stones of different physical properties," Urological Research 38(4):315-319, 2010.
Ferri, M., et al., "On the Evaluation of the Suitability of the Materials Used to 3D Print Holographic Acoustic Lenses to Correct Transcranial Focused Ultrasound Aberrations," Polymers 2019, 11(9), 1521, 25 pages.
Ferri, M., et al., "Enhanced Numerical Method for the Design of 3-D-Printed Holographic Acoustic Lenses for Aberration Correction of Single-Element Transcranial Focused Ultrasound," Ultrasound in Medicine and Biology 45(3):867-884, 2019.
Gao, H., et al., "Acoustic focusing by symmetrical self-bending beams with phase modulations," Applied Physics Letters, vol. 108, No. 7, 2016, 5 pages.
Hadimioglu, B., et al., "High-Efficiency Fresnel Acoustic Lenses," IEEE Ultrasonics Symposium, pp. 579-582, 1993.
Harper, J.D., et al., "Focused Ultrasound to Expel Calculi from the Kidney: Safety and Efficacy of a Clinical Prototype Device," The Journal of Urology 190:1090-1095, 2013.

(56) References Cited

OTHER PUBLICATIONS

He, J., et al., "Multitarget Transcranial Ultrasound Therapy in Small Animals Based on Phase-Only Acoustic Holographic Lens," in IEEE Transactions on Ultrasonics, Ferroelectrics, and Frequency Control 69(2):662-671, 2022.
Hsiao, Y.-H., et al., "Clinical Application of High-Intensity Focused Ultrasound in Cancer Therapy," Journal of Cancer 7(3):225-231, 2016.
Hunter, C., et al., "Evaluation of in vitro burst wave lithotripsy exposure conditions," Scientific Program of 35th World Congress of Endourology Program Book and Abstracts, BRPS4: Bench to Bedside: The Science of Stones II—A37—Journal of Endourology, vol. 31, No. S2, paper BRPRS4-20, 2017.
Hiwang, E.Y., et al., "Variables controlling contrast generation in a urinary bladder model," The Journal of the Acoustical Society of America 103(6):3706-3716, 1998.
Ikeda T., et al., "Cloud cavitation control for lithotripsy using high intensity focused ultrasound," Ultrasound in Medicine Biology 32(9):383-1397, 2006.
Jeong, J.S., et al., "Extended Necrosis by Using Dual-Curved Therapeutic Transducer for Noninvasive HIFU Surgery," 2011 IEEE International Ultrasonics Symposium, Orlando, Florida, 2011, pp. 2321-2324.
Jiménez-Gambín, S., et al., "Generating Bessel beams with broad depth-of-field by using phase-only acoustic holograms," Scientific Reports 9:20104, 2019, 13 pages.
Jiménez-Gambín, S., et al., "Holograms to Focus Arbitrary Ultrasonic Fields through the Skull," Physical Review Applied vol. 12, Issue 1, 2019, 14 pages.
Kim, G., et al., "Poroelastic microlattices for underwater wave focusing," Extreme Mechanics Letters vol. 49, 2021, 6 pages.
Kim, J., et al., "Acoustic holograms for directing arbitrary cavitation patterns," Applied Physics Letters vol. 118, No. 5, 2021, 2021, 7 pages.
Kim, J., et al., "Holographic acoustic admittance surface for acoustic beam steering, " Applied Physics Letters, vol. 115, No. 19. 2019, 6 pages.
Kim, Y., et al., "Rapid Prototyping Fabrication of Focused Ultrasound Transducers," IEEE Transactions on Ultrasonics Ferroelectrics, and Frequency Control 61(9):1559-1574, 2014.
Krimholtz, R., et al., "New equivalent circuits for elementary piezoelectric transducers," Electronics Letters 6 (13):398-399, 1970.
Lee, S., et al., "Preclinical study to improve microbubble-mediated drug delivery in cancer using an ultrasonic probe with an interchangeable acoustic lens," Scientific Reports 11:12654, 2021, 10 pages.
Lévesque, D., et al., "Performance of Ultrasonic Imaging With Frequency Domain SAFT (F-SAFT)," Industrial Materials Institute, National Research Council Canada, Boucherville, Quebec, Canada, Sep. 2004, 8 pages.
Li, X.-S., "Modulation of acoustic self-accelerating beams with tunable curved metasurfaces," Applied Physics Letters, vol. 118, No. 2, 2021, 6 pages.
Li, Z., et al., "Acoustic Hole-Hologram for Ultrasonic Focusing With High Sensitivity," in IEEE Sensors Journal 21(7):8935-8942, 2021.
Litwin, M.S., and C.S. Saigal, "Urologic Diseases in America 2012," Washington, DC US Gov. Print. Office; NIH Publ. No. 12-7865, Tables: 11-2-11-42, 2012.
Liu, Y., and P. Zhong, "BegoStone—a new stone phantom for shock wave lithotripsy research (L)," The Journal of Acoustical Society of America 112(4):1265-1268, 2002.
Maréchal, P., et al., "Effect of Acoustical Properties of a Lens on the Pulse-Echo Response of a Single Element Transducer," 2004 IEEE International Ultrasonics Symposium Ferroelectrics, and Frequency Control Joint 50th Anniversary Conference, Montreal, Quebec, Canada, vol. 3, pp. 1651-1654.
Marzo, A., et al., "Holographic acoustic elements for manipulation of levitated objects," Nature Communications, vol. 6, No. 1, 9661, 2015, 7 pages.
Maslakowski, M.S., et al., "The Characterization and Assembly of an Efficient, Cost Effective Focused Ultrasound Transducer," 2020 IEEE 14th Dallas Circuits and Systems Conference (DCAS), Dallas, Texas, 2020, 6 pages.
Maxwell, A. D., et al., "Fragmentation of Urinary Calculi In Vitro by Burst Wave Lithotripsy.," The Journal of Urology 193(1): 338-44, 2015.
May, P.C., et al., "Detection and Evaluation of Renal Injury in Burst Wave Lithotripsy Using Ultrasound and Magnetic Resonance Imaging," Journal of Endourology 31(8):786-792, 2017.
Mayo Clinic, "Kidney stones diagnosis and treatment" [internet], [cited Mar. 18, 2018], 9 pages.
McDonald, B., "surf2stl—File Exchange—MATLAB Central." [Online]. Available: https://www.mathworks.com/matlabcentral/fileexchange/4512-surf2stl, [Accessed: Jul. 22, 2018], 1 page.
Melde, K., et al., "Holograms for acoustics," Nature, vol. 537, No. 7621, pp. 518-522, 2016.
Mellin, S., and G. Nordin, "Limits of scalar diffraction theory and an iterative angular spectrum algorithm for finite aperture diffractive optical element design," Optics Express 8(13):705-722, 2001.
National Kidney Foundation Inc. , "Kidney Stones" [internet], National Kidney Foundation Inc. [cited Mar. 18, 2018], 6 pages.
National Kidney Foundation Inc. , "Kidney Stone Treatment: Shock Wave Lithotripsy" [internet], National Kidney Foundation Inc. [cited Mar. 18, 2018 ], 6 pages.
Nikolić, V., and B. Kaltenbacher, "Sensitivity Analysis for Shape Optimization of a Focusing Acoustic Lens in Lithotripsy," Applied Mathematics & Optimization 76(2): 261-301, 2017.
Oberlin, D.T., et al., "Contemporary Surgical Trends in the Management of Upper Tract Calculi," The Journal of Urology, 193(3):880-884, 2015.
Pishchalnikov, Y.A., et al., "Cavitation selectively reduces the negative-pressure phase of lithotripter shock pulses," Acoustics Research Letters Online 6(4):280-286, 2005.
Pishchalnikov, Y.A., and J.A. McAteer, "Cavitation-induced streaming in shock wave lithotripsy," Proceedings of Meetings on Acoustics, vol. 19, 075032, pp. 1-9; The Journal of Acoustical Society of America 133(5):3315-3315, 2013.
Pishchalnikov, Y.A., et al., "Why Stones Break Better at Slow Shockwave Rates Than at Fast Rates: In Vitro Study With a Research Electrohydraulic Lithotripter," Journal of Endourology 20(8):537-41, 2006.
Pishchalnikov, Y.A., et al. "Bubble proliferation in shock wave lithotripsy," The Journal of Acoustical Society of America 121(5):3081, 2007.
Pishchalnikov, Y.A., and J.A. McAteer, "Gas content of the medium surrounding a stone has a significant effect on the efficiency of stone breakage in shock wave lithotripsy.," The Journal of Acoustical Society of America vol. 127, No. 3, 1761, 2010.
Randad, A.P., "Design, Fabrication and Characterization of Ultrasound Transducers for Fragmenting Large Renal Calculi," [online], master's thesis, University of Washington, 2018 [retrieved Sep. 26, 2019] Retrieved from <University of Washington ResearchWorks Archive, <https://digital.lib.washington.edu/researchworks/handle/1773/43102>; figure 3/1, pp. 32, 51, and 78.
Randad, A., et al., "Design, fabrication, and characterization of broad beam transducers for fragmenting large renal calculi with burst wave lithotripsy," The Journal of Acoustical Society of America 148(1):44-50, 2020.
Randad, A.P., et al., "Design of a Transducer for Fragmenting Large Kidney Stones Using Burst Wave Lithotripsy," Proceedings of Meetings on Acoustics 35(1):1-11, 2018.
Rassweiler, J.J., et al., "Shock Wave Technology and Application: An Update," European Urology 59(5):784-796, 2011.
Rosnitskiy, P.B., et al., "Design of HIFU Transducers for Generating Specified Nonlinear Ultrasound Fields," in IEEE Transactions on Ultrasonics, Ferroelectrics, and Frequency Control 64(2):374-390, 2017.
Sallam, A., et al., "Theoretical and experimental investigations on metallic acoustic lenses," Proc. SPIE vol. 11588, Active and Passive Smart Structures and Integrated Systems XV, 1158807, Mar. 2021.

(56) References Cited

OTHER PUBLICATIONS

Samoudi, M.A. et al., "Computational modeling of a single-element transcranial focused ultrasound transducer for subthalamic nucleus stimulation," Journal of Neural Engineering, vol. 16, No. 2, 026015, 2019, 13 pages.

Sapozhnikov, O.A., "A mechanistic analysis of stone fracture in lithotripsy.," The Journal of Acoustical Society of America 121(2):1190-202, 2007.

Sapozhnikov, O.A., et al., "Effect of overpressure and pulse repetition frequency on cavitation in shock wave lithotripsy," The Journal of Acoustical Society of America 112(3):1183-1195, 2002.

Scales, C.D., et al., "Prevalence of kidney stones in the United States," Urologic Diseases in America Project, European Urology 62(1):160-5, 2012.

Simon, J.C., et al., "Some Work on the Diagnosis and Management of Kidney Stones with Ultrasound," Acoustics Today 13(4):52-59, 2017.

Sonic Concepts, Inc., Therapy Transducers, <https://sonicconcepts.com/therapy-transducers/>, 2021.

Sorensen, M.D., et al., "Focused ultrasonic propulsion of kidney stones: review and update of preclinical technology.," Journal of Endourology 27(10):1183-1186, 2013.

Souquet, J., et al., "Design of Low-Loss Wide-Band Ultrasonic Transducers for Noninvasive Medical Application," IEEE Transactions on Sonics Ultrasonics 26(2):75-80, 1979.

Spirou, G.M., et al., "Optical and acoustic properties at 1064 nm of polyvinyl chloride-plastisol for use as a tissue phantom in biomedical optoacoustics," Physics in Medicine and Biology 50(14):N141-N153, 2005.

Srinivas, V., and R.L. Harne, "Acoustic wave focusing by doubly curved origami-inspired arrays," Mechanical Engineering, Journal of Intelligent Material Systems and Structures 31(8)1041-1052, 2020.

Starritt, H.C., et al., "An experimental investigation of streaming in pulsed diagnostic ultrasound beams," Ultrasound in Medical and biology 15(4):363-373, 1989.

Suomi, V., et al., "Full Modeling of High-Intensity Focused Ultrasound and Thermal Heating in the Kidney Using Realistic Patient Models," IEEE Transactions on Biomedical Engineering 65(5):969-979, 2018.

Thomas, G.P.L, et al., "Parametric Shape Optimization of Lens-Focused Piezoelectric Ultrasound Transducers," IEEE Transactions on Ultrasonics, Ferroelectrics, and Frequency Control 65(5):844-850, 2018.

Tiselius, H.-G., and A. Andersson, "Stone Burden in an Average Swedish Population of Stone Formers Requiring Active Stone Removal: How Can the Stone Size Be Estimated in the Clinical Routine?" European Urology 43:275-281. 2003.

Jeno, A., et al., "Relation of Spontaneous Passage of Ureteral Calculi to Size," Urology 10(6):544-546, 1977.

Upsdell, S.M., et al., "Diuretic-induced urinary flow rates at varying clearances and their relevance to the performance and interpretation of diuresis renography.," British Journal of Urology 61(1):14-18, 1988.

Wang, M., et al., "Design and fabrication of diffractive microlens and analysis of optical characteristics," Proceedings of the SPIE, vol. 7657, id. 765717 (2010).

Worcester, E.M. and F.L. Coe, "Nephrolithiasis," Primary Care: Clinics in Office Practice 35(2):369-391, 2008.

Yoshida, S. and M. Yamamoto, "Design and Evaluation of Diffractive Optical Elements: Optimization by Using Iterative Angular Spectrum Approach and Evaluation Based on Vector Diffraction Theory," in Baldini, F., et al. (eds.), Optical Sensors 2009. • Proceedings of SPIE (The International Society for Optical Engineering), 7356:73561Z-1-73561Z-8, May 2009.

Zhong, P., et al., "Recent Developments in SWL Physics Research," Journal of Endourology 13(9):611-617, 1999.

Zhou, Q., et al., "High efficiency acoustic Fresnel lens," Journal of Physics D: Applied Physics, vol. 53, No. 6, 065302, 2019, 7 pages.

Zwaschka, T.A., et al., "Combined Burst Wave Lithotripsy and Ultrasonic Propulsion for Improved Urinary Stone Fragmentation," Journal of Endourology 32(4):344-349, 2018.

Armstrong, J.P. K. et al., "Engineering Anisotropic Muscle Tissue using Acoustic Cell Patterning," Adv. Mater. 2018, 30, 1802649, pp. 1-7.

Armstrong, J. P. K. and M. M. Stevens. "Using Remote Fields for Complex Tissue Engineering," Trends in Biotechnology, Mar. 2020, vol. 38, No. 3, pp. 254-263 https://doi.org/10.1016/j.tibtech.2019.07.005.

Baudoin M. et a., "Spatially selective manipulation of cells with single-beam acoustical tweezers," Nature Communications; 202011:4244, pp. 1-10 https://doi.org/10.1038/s41467-020-18000-y.

Chansoria, P. and R. Shirwaiker, "3D bioprinting of anisotropic engineered tissue constructs with ultrasonically induced cell patterning," Elsevier: Additive Manufacturing 32 (2020) 101042, pp. 1-12.

Chansoria, P. and R. Shirwaiker, "Characterizing the Process Physics of Ultrasound-Assisted Bioprinting," Scientific Reports 2019 9: 13889, p. 1-17 https://doi.org/10.1038/s41598-019-50449-w.

Chansoria, P. et al., Ultrasound-assisted biofabrication and bioprinting of preferentially aligned three-dimensional cellular constructs, Biofabrication 11 (2019) 035015, pp. 1-18.

Cheng, K. W. et al., "Fast three-dimensional micropatterning of PC12 cells in rapidly crosslinked hydrogel scaffolds using ultrasonic standing waves," 2020 Biofabrication 12 015013.

Dardikman-Yoffe, G. et al. "High-resolution 4-D acquisition of freely swimming human sperm cells without staining," Sci. Adv. 2020; 6: eaay7619 Apr. 10, 2020.

Ding, X. et al., "Tunable patterning of microparticles and cells using standing surface acoustic waves," Lab Chip, 2012, 12, 2491-2497.

Gesellchen, F. et al., "Cell patterning with a heptagon acoustic tweezer—application in neurite guidance," Lab Chip, 2014, 14, 2266.

Gu, Y. et al., "Acoustofluidic Holography for Micro- to Nanoscale Particle Manipulation," ACS Nano 2020, 14, 14635-14645.

Hampson, M., "Ultrasonic Holograms: Who Knew Acoustics Could Go 3D? Imaging and other medical applications waiting in the wings," News Sensors, Feb. 3, 2021.

Kim, H. N., "Patterning Methods for Polymers in Cell and Tissue Engineering," Annals of Biomedical Engineering, vol. 40, No. 6, Jun. 2012 (2012) pp. 1339-111326135 5.

Imashiro, C.; Shimizu, T. "Fundamental Technologies and Recent Advances of Cell-Sheet-Based Tissue Engineering," Int. J. Mol. Sci. 2021, 22,425. https://doi.org/ 10.3390/ijms22010425.

Joenathan, C. et al., "Lateral shear interferometer using multiplexed holographic lenses and spatial Fourier transform: varying spectrum position and phase fluctuations," Optical Engineering 52(8), 084103 (Aug. 2013).

Joenathan, C. et al., "Novel and simple lateral shear interferometer with holographic lens and spatial Fourier transform," Optical Engineering 51(7), 075601 (Jul. 2012).

Koo, K-i et al., "Acoustic Cell Patterning in Hydrogel for Three-Dimensional Cell Network Formation," Micromachines 2021, 12, 3. https://dx.doi.org/10.3390/ mi12010003.

Ma, Z. et al., "Acoustic Holographic Cell Patterning in a Biocompatible Hydrogel," Adv. Mater. 2020, 32, 1904181, pp. 1-6.

Murugan, Ph.D., R. and S. Ramakrishna, Ph.D., "Design Strategies of Tissue Engineering Scaffolds with Controlled Fiber Orientation," Tissue Engineering vol. 13: No. 8, 2007, Mary Ann Liebert, Inc., DOI: 10.1089/ Dten.2006.0078.

Physics World, "Holographic lenses focus ultrasound in the brain," Apr. 18, 2019.

Ren, X et al., "Particle Trapping in Arbitrary Trajectories Using First-Order Bessel-Like Acoustic Beams," Physical Review Applied 15, 054041 (2021).

Shi, J. et al., "Acoustic tweezers: patterning cells and microparticles using standing surface acoustic waves (SSAW)," Lab Chip, 2009, 9, 2890-2895.

Shipman, M. "Ultrasound Aligns Living Cells inBioprinted Tissues," Apr. 10, 2019; 4-min. read.

(56) References Cited

OTHER PUBLICATIONS

Yang, S. et al., "Harmonic acoustics for dynamic and selective particle manipulation," Nature Materials, vol. 21, May 2022, 540-546.
Stevens, M. M. et al., "Direct patterning of mammalian cells onto porous tissue engineering substrates using agarose stamps," Elsevier: Biomaterials 26 (2005) 7636-7641.
Tian, Z. et al., "Generating multifunctional acoustic tweezers in Petri dishes for contactless, precise manipulation of bioparticles," Tian et al., Sci. Adv. 2020; 6 : eabb0494 Sep. 9, 2020.
Wang, X. et al., "A method for solvent-free fabrication of porous polymer using solid-state foaming and ultrasound for tissue engineering applications," Elseier: Biomaterials 27 (2006) 1924-1929.
Dalecki, D. and D. C. Hocking, "Ultrasound Technologies for Biomaterials Fabrication and Imaging," Annals of Biomedical Engineering, vol. 43, No. 3, Mar. 2015 (2014) pp. 747-761; DOI: 10.1007/s10439-014-1158-6.
Falconnet, D. et al., "Surface engineering approaches to micropattern surfaces for cell-based assays," Elsevier: Biomaterials 27 (2006) 3044-3063.
Gjorevski, N. et al., "Designer matrices for intestinal stem cell and organoid culture," Nature vol. 539, Nov. 2016, 560-576; doi: 10.1038/nature20168.
Hitchock, T. and L. Niklason, "Lymphatic Tissue Engineering Progress and Prospects," Ann NY Acad Sci. 2008; 1131: 44-49. doi: 10.1196/annals.1413.004.
Jaklenec, Ph.D., A et al., Progress in the Tissue Engineering and Stem Cell Industry "Are we there yet?" Tissue Engineering: Part B, vol. 18, No. 3, 2012, 155-167; DOI: 10.1089/ten.teb.2011.0553.
Jeon, H. et al., "Directing cell migration and organization via nanocrater-patterned cell repellent interfaces," Nat Mater. Sep. 2015; 14(9): 918-923. doi:10.1038/nmat4342.
Koo, K. et al., "Acoustic Cell Patterning in Hydrogel for Three-Dimensional Cell Network Formation," Micromachines 2021, 12, 3. https://dx.doi.org/10.3390/ mi12010003.
Olson, J. L. et al., "Tissue Engineering: Current Strategies and Future Directions," Chonnam Med J 2011 ;47: 1-13; DOI: 10.4068/cmj.2011.47.1.1.
Rajagopalan, P. et al., "Direct Comparison of the Spread Area, Contractility, and Migration of balb/c 3T3 Fibroblasts Adhered to Fibronectin- and RGD-Modified Substrata," Biophysical Journal vol. 87 Oct. 2004 2818-2827.
Shanjani, PhD., Y. et al., "Acoustic Patterning of Growth Factor for Three-Dimensional Tissue Engineering," Tissue Engineering: Part A, vol. 26, Nos. 11 and 12, 2020, 602-612; DOI: 10.1089/ten.tea.2019.0271.
Young, J. L. et al., Nanoscale and mechanical properties of the physiological cell-ECM microenvironment, Elsevier: Experimental Cell Research 343 (2016) 3-6.
Dennis Li et al., "Design of an acoustic metamaterial lens using genetic algorithms," Oct. 1, 2012, The Journal of the Acoustical Society of America, 132, 4, pp. 2823-2833 (Year: 2012).
M. Bakhtiari-Nejad, "Passive metamaterial-based acoustic holograms in ultrasound energy transfer systems," Mar. 15, 2018, Proc. SPIE 10595, Active and Passive Smart Structures and Integrated Systems XII (Year: 2018).
J. Xia et al., "Broadband Tunable Acoustic Asymmetric Focusing Lens from Dual-Layer Metasurfaces," Jul. 17, 2018, Physical Review Applied , 10, pp. 014016-1 to 014016-12 (Year: 2018).
International Search Report and Written Opinion, mailed Nov. 5, 2019, issued in corresponding International Application No. PCT/US2019/046501, filed Aug. 14, 2019, 9 pages.
McDonald, B., "Surf2stl," MATLAB Central File Exchange, 2021, https://www.mathworks.com/matlabcentral/fileexchange/4512-surf2stl (Retrieved Feb. 14, 2021), 8 pages.
Randad, A., "Design, Fabrication and Characterization of Ultrasound Transducers for Fragmenting Large Renal Calculi," master's thesis, University of Washington, Seattle, Washington, Nov. 2018, < University of Washington Research Works Archive, https://digital.lib.washington.edu/researchworks/handle/1773/43102> (retrieved on Sep. 26, 2019, 104 pages.
Suomi. V., et al., "Full Modeling of High-Intensity Focused Ultrasound and Thermal Heating in the Kidney Using Realistic Patient Models," IEEE Transactions on Biomedical Engineering, 65(5):969-979, May 2018.

\* cited by examiner

CROSS-SECTION C-C

CROSS-SECTION D-D

NON-PLANAR HOLOGRAPHIC BEAM SHAPING LENSES FOR ACOUSTICS

STATEMENT OF GOVERNMENT LICENSE RIGHTS

This invention was made with government support under Grant No. P01 DK043881, awarded by the National Institutes of Health. The government has certain rights in the invention.

BACKGROUND

Acoustic waves can transfer energy that causes heating of targets placed in an acoustic field, imparts radiation forces on object placed in the field, and induces mechanical effects that can damage or break solids including soft tissue or even solids such as kidney stones. Therefore, ultrasound has therapeutic applications such as removal of tumors, drug delivery, tissue heating, and manipulation of urinary stones or foreign objects toward their removal. These applications are achieved by developing the ultrasound or acoustic beam shape. By controlling and precisely shaping the acoustic beam, we can target a specific region in the body for treatment. For instance, the shaping of the ultrasound beam allows focusing of the acoustic energy to a confined region of interest where the tumor tissue is targeted for treatment, the accelerated exchange of ultrasound energy for tissue heating, the enhancement of drug delivery to a specific region, and creation of pressure cages that can surround and manipulate objects in the body.

The ability to shape and synthesize acoustic beam to a specific geometry based on particular application can be achieved by two methods: multi-element arrays (phased arrays) or holographic lenses. Multi-element arrays are expensive to fabricate, require long wait times to manufacture, and require complex driving electronic equipment. Generally, holographic lenses are relatively affordable, simple to integrate, quick to fabricate, and allow for more precise control of the phase distribution. However, holographic lenses tend to be relatively thick once integrated with a curved transducer. Therefore, when a beam shaping is required to concentrate the acoustic energy over a small, confined space of the transducer aperture, the relatively thick lens leads to high losses of acoustic energy and inability to precisely shape the ultrasound beam. Accordingly, there remains a need improved holographic lenses and methods for their use.

SUMMARY

This summary is provided to introduce a selection of concepts in a simplified form that are further described below in the Detailed Description. This summary is not intended to identify key features of the claimed subject matter.

Briefly, the inventive technology is directed to generating an ultrasound beam to treat objects in a body (e.g., stones, calcifications, tumors, etc.). Some examples of such treatment are tissue ablation, lithotripsy, repositioning of stones or stone fragments, etc.

In different embodiments, the shape and volume of the ultrasound treatment area is controlled by a customizable lens. The customizable lens may be designed using an iterative angular spectrum approach (IASA). In some embodiments, the customizable lens is an acoustic diffractive lens (also referred to as "lens," "customizable lens," "diffractive lens," "holographic lens," "non-planar holographic lens" or "curved holographic lens") that generates phase offsets and redirection in the wave front as the ultrasound waves transit the lens.

When a holographic lens is mated to an ultrasonic transducer having a prescribed amplitude and frequency of the ultrasound, the customizable lens develops a pattern of phases that, in turn generates a target beam pattern of pressure amplitude and phase at the target focal surface. Furthermore, in some embodiments the amplitude/phase distribution of the ultrasound may be controllable in several different planes of ultrasound propagation to produce different patterns of ultrasound pressure amplitudes and phases at these target planes.

In some embodiments, the ultrasound beam creates amplitude/phase fields that apply radiation force in a desired direction. For example, the ultrasound beam may create a 2-dimensional or 3-dimensional pressure well around an object to trap it in a position. In other embodiments, the pressure field can have a phase gradient imposed, therefore moving a stone or other solid object along a gradient in a predetermined path. Alternatively, a stone or other object may be blocked from moving down a path or into a certain area by a beam that forms a barrier based on the ultrasound pressure amplitude or phase gradient.

In some embodiments, the customizable holographic lens is curved along its principal plane such that the holographic lens conforms to the mating surface of the transducer. For example, for the transducer having a concave outside surface, the holographic lens may be correspondingly shaped such that the smooth surface of the holographic lens (i.e., the surface that is free of holographic features) mates with the outside surface of the transducer or with the interface material at the transducer. The holographic features on the opposite, non-mating side of the lens face the target area of the body. For the transducer having a wavy outside surface, the holographic lens may be correspondingly shaped to mate with the outside surface of the transducer or with the interface material.

By using a holographic lens having a relatively uniform thickness (other than the thickness variations caused by the holographic features themselves) and a principal plane that follows the curvature of the mating surface of the transducer, the acoustic losses can be reduced and ultrasound targeting can be improved. Such improvements are at least in part based on reduction of the overall thickness of the holographic lens, which in turn reduces energy dissipation and improves targeting of the curved holographic lens (non-planar holographic lens). Improvements are also based on the reduction of discontinuities on the surface with the holographic features, which in turn improves the accuracy of the desired results of phase and or pressure.

In some embodiments, the target treatment areas are selectable by adjusting the frequencies of the transmitted ultrasound. In some embodiments, the customizable lens is produced by three-dimensional (3D) additive printing. The customizable lens may be attached-to and removed-off the transducer with a quick-change holding mechanism and a temporary interface.

In one embodiment, an ultrasonic therapy system configured to apply ultrasound to a target in a body includes: an ultrasonic transducer configured to generate the ultrasound; and a curved holographic lens configured to focus the ultrasound onto a focal area of a target that is an object or a portion of the object in the body. The curved holographic lens is designed and produced based on the target, and where the curved holographic lens is curved to mate with a front surface of the ultrasonic transducer.

In one aspect, the curved holographic lens is designed based on an iterative angular spectrum approach (IASA) and Rayleigh integral.

In another aspect, the target is defined by at least one acquired image of the object in the body.

In one aspect, the ultrasonic transducer is a multi-element ultrasonic transducer.

In one aspect, a curvature of the front surface of the ultrasonic transducer is a spherical, parabolic or elliptical curvature.

In another aspect, the front surface of the ultrasonic transducer includes more than one curvature.

In one aspect, a curvature of the front surface of the ultrasonic transducer is a non-constant curvature disposed along multiple directions.

In one aspect, the curved holographic lens is a three-dimensional (3D) printed lens.

In one aspect, the ultrasound is configured to produce at least one of a thermal therapy, a histotripsy, a lithotripsy, a drug delivery, a diagnostic imaging, an image guidance, a microbubble manipulation, and a manipulation and removal of urinary stone fragments at the target.

In one embodiment, a method for applying an ultrasound to a target in a body includes defining, based on the target, an intermediate plane that is a customizable holographic velocity or pressure plane. The target is an object or a portion of the object in the body, and the intermediate plane is a flat, two-dimensional surface. The method also includes defining a customizable holographic lens as a curved holographic lens by back-propagating the intermediate plane to a curved surface that matches a front surface of an ultrasonic transducer. The method further includes defining a thickness of the curved holographic lens in a direction normal to the front surface of the ultrasonic transducer using a phase from the ultrasonic transducer to define the thickness; generating the ultrasound by the ultrasonic transducer; and focusing the ultrasound onto a focal area of the object by the curved holographic lens.

In one aspect, the method also includes acquiring an image of the object, where the curved holographic lens is defined at least in part based on the image of the object.

In one aspect, the method also includes manufacturing the curved holographic lens by three-dimensional (3D) additive-printing.

In another aspect, the ultrasonic transducer is a single element transducer.

In one aspect, manufacturing the curved holographic lens by machining or injection molding.

In one aspect, the method also includes: applying an interface material to a surface of the curved holographic lens; mating the customizable lens with the ultrasonic transducer via the interface material; and after focusing the ultrasound onto the focal area, removing the curved holographic lens from the ultrasonic transducer.

In one aspect, focusing the ultrasound onto the focal area of the object includes focusing ultrasound pressure amplitude distribution or ultrasound pressure phase distribution over the focal area.

In one aspect, a curvature of the front surface of the ultrasonic transducer is a spherical, parabolic or elliptical curvature.

In another aspect, the front surface of the ultrasonic transducer includes more than one curvature.

In yet another aspect, a curvature of the front surface of the ultrasonic transducer is a non-constant curvature disposed along multiple directions.

DESCRIPTION OF THE DRAWINGS

The foregoing aspects and many of the attendant advantages of the inventive technology will become more readily appreciated as the same are understood with reference to the following detailed description, when taken in conjunction with the accompanying drawings, where.

DETAILED DESCRIPTION

In order to better understand the technical solutions of the present disclosure, the embodiments of the present disclosure are described in detail below with reference to the accompanying drawings. It should be clear that the described embodiments are only a part of the embodiments of the present disclosure, but not all of the embodiments. Based on the embodiments in the present disclosure, all other embodiments obtained by those of ordinary skill in the art fall within the protection scope of the present disclosure.

The terms used in the embodiments of the present disclosure are only for the purpose of describing specific embodiments, and are not intended to limit the present disclosure. As used in the embodiments of this application and the appended claims, the singular forms "a," "the," and "the" are intended to include the plural forms as well, unless the context clearly dictates otherwise.

It should be understood that the term "and/or" used in this document is only an association relationship to describe the associated objects, indicating that there can be three relationships, for example, A and/or B, which can indicate that A alone, A and B, and B alone. The character "/" in the present description generally indicates that the related objects are an "or" relationship.

It should be understood that although the terms 'first', 'second', and 'third' can be used in the present disclosure to describe thin film transistors, these thin film transistors should not be limited to these terms. These terms are used only to distinguish the thin film transistors from each other.

In the context of this disclosure, the terms "about," "approximately," "generally" and similar mean +/−5% of the stated value.

Figure 1:
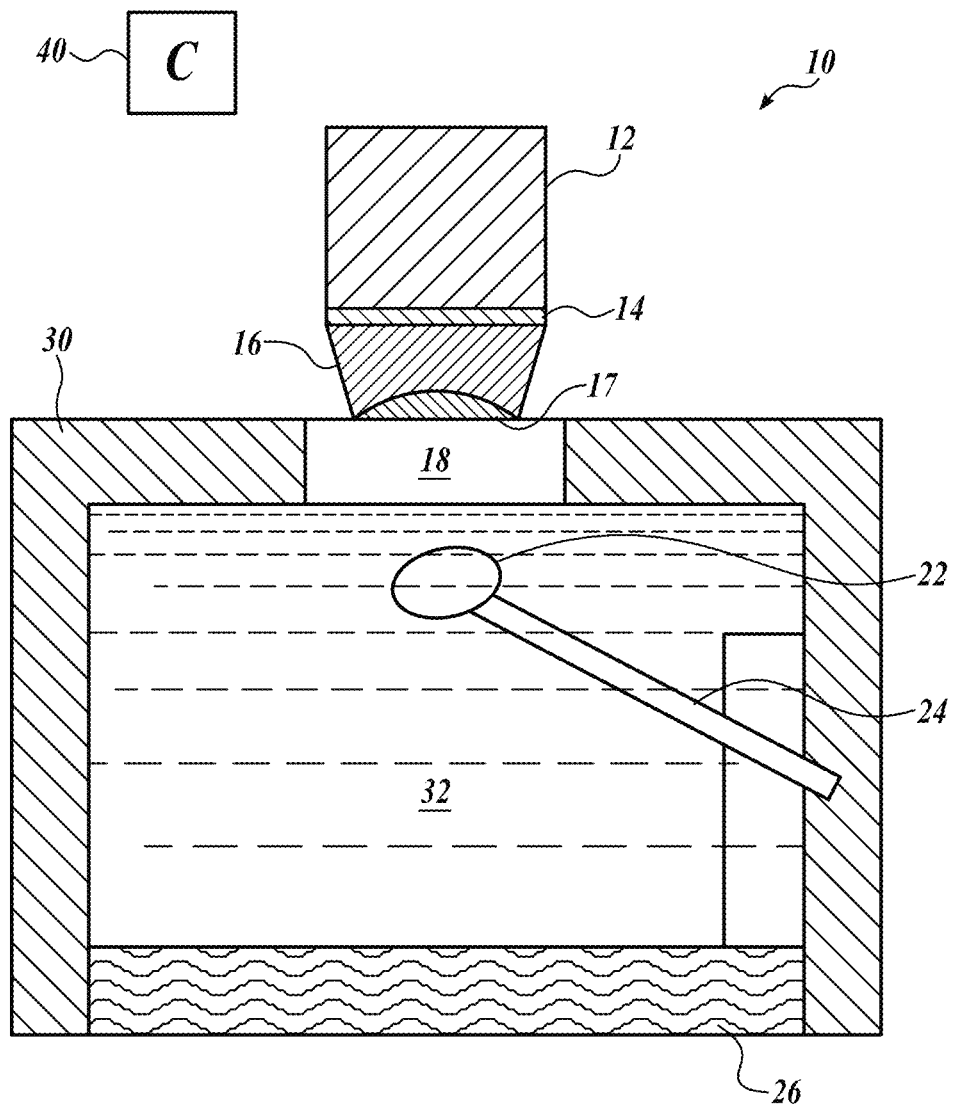
FIG. 1 is a side plan view of an ultrasound system in accordance with conventional technology.

FIG. 1 is a side plan view of an ultrasound system 10 in accordance with conventional technology. The ultrasound system 10 is a test system that includes a housing 30 that is filled with a medium 32 (typically water) that facilitates transmission of the ultrasound within the system 10. The ultrasound system 10 includes a test target 22 representing, for example, a hypothetical calcification or tumor in a body. The target 22 is held by a target holder 24.

A transducer 12 generates vibrations at ultrasound frequencies (e.g., from about 20 kHz to about 10 MHz). The transducer 12 can be a piezoelectric element that expands and shrinks with changing electrical polarity applied to the transducer. Such a change in electrical polarity can be applied by an alternating current (AC) at a target ultrasound frequency. An interface 14 attaches a lens to the transducer 14. The interface 14 is typically a permanent epoxy or other suitable strong adhesive. In operation, the lens 16 focuses the ultrasound generated by the transducer 12 through an acoustic window 18 onto a target 22. Much like optical systems, acoustic waves obey Snell's law. For that reason, ultrasound can be shaped by the lens 16 in the path of a propagating acoustic wave. Acoustic lenses (refractive lenses) bend the propagating wave in proportion to the ratio of indices of refraction of the lens and of a target medium, such as biological tissue. The index of refraction is a material property, depending on the speed of sound in the material.

A coupling 17 (e.g., gel, oil, etc.) provides acoustic coupling for the ultrasound propagating toward the target 22. The ultrasound system 10 includes an absorber 26 that prevents ultrasound from escaping into the environment. The operation of the transducer 12 can be controlled by a controller 40.

Figure 2:
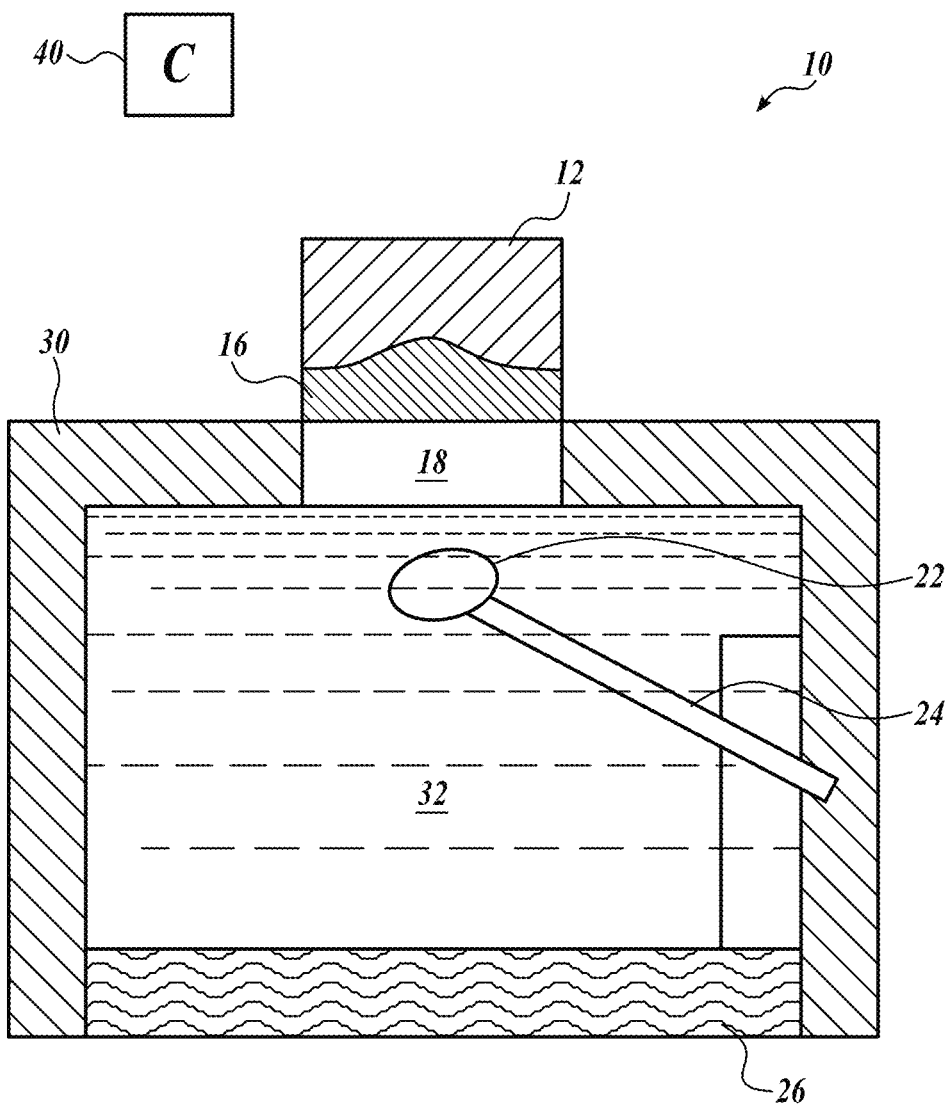
FIG. 2 is a side plan view of an ultrasound system in accordance with conventional technology.

FIG. 2 is a side plan view of an ultrasound system 10 in accordance with conventional technology. The illustrated conventional system 10 includes a holographic lens 16. However, the illustrated holographic lens 16 is relatively thick in the middle of the transducer 12, therefore increasing the acoustic losses and degrading targeting precision of the ultrasound system 10.

A person of ordinary skill would know that one of the challenges in developing ultrasound instruments for moving and breaking urinary tract stones is generating the appropriate acoustic pressure and beam shape to effectively apply force to or fragment the stone. For example, if a beam is too narrow, it may not fragment a stone because it does not impart enough energy on the entire stone. On the other hand, if a beam is too wide, ultrasound energy is wasted on collateral tissue. Therefore, ultrasound focusing is often necessary to achieve sufficient pressure on the stone.

Figure 3:
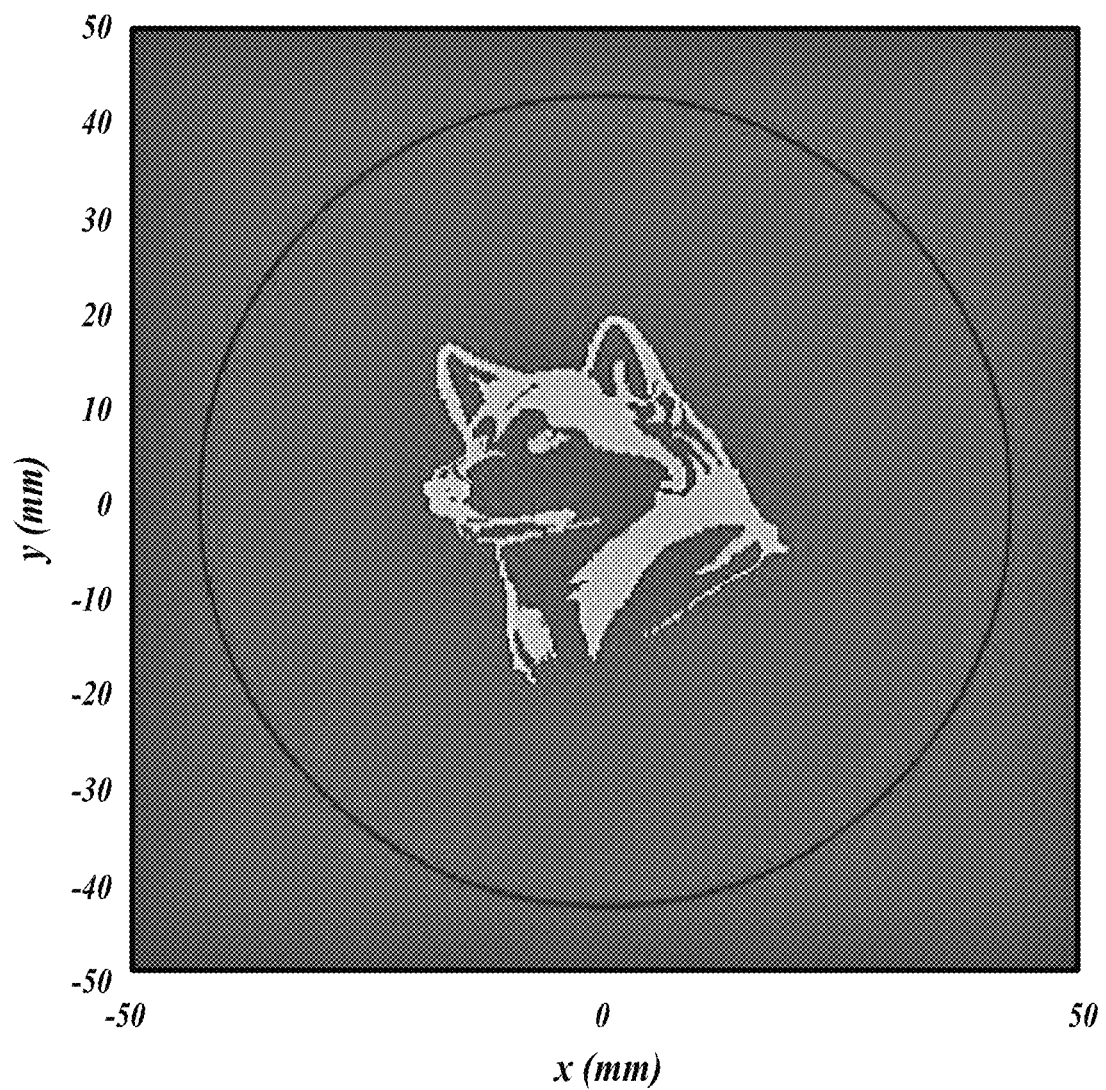
FIG. 3 is a view of a sample target object.

FIG. 3 is a view of a sample target object. The horizontal and vertical axes represent the target size in millimeters. Illustrated sample target image is 32 mm away from the source of the ultrasound. The illustrated target image is binary, the bright areas representing the maximum target pressure and dark areas representing zero target pressure. However, in different embodiments non-binary distributions of target pressure amplitude or phase may be used. The circle that is around the image shows the outline of the transducer aperture (which is in the 0 mm plane). The combination of transducer and lens attempts to re-create the illustrated pressure field at 32 mm distance from the source of the ultrasound. A method of designing such customizable lens is described with reference to FIG. 5 below.

Figure 4:
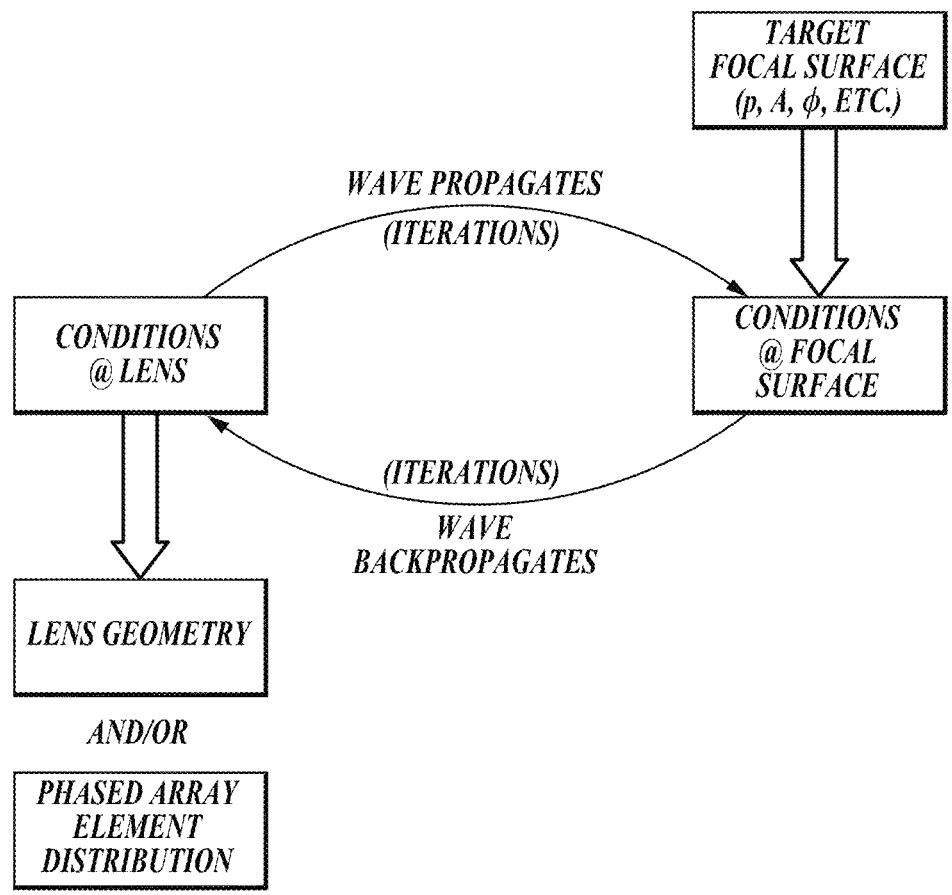
FIG. 4 is a schematic diagram of a method for designing a customizable lens in accordance with an embodiment of the present technology.

FIG. 4 is a schematic diagram of a method for designing a customizable lens in accordance with an embodiment of the present technology. In operations, the lens stimulates additive and destructive interference in a propagating wave front to generate a desired pressure and/or phase pattern at a target focal surface. The iterative angular spectrum approach (IASA) develops precise phase mappings for the lenses, which in turn provide a physical design for the lens geometry. As explained with reference to the conventional technology, typical approaches to lens design, such as the Fresnel approximation, fail to produce the desired pressure pattern with sufficient precision when the feature size in desired pressure pattern approaches the wavelength of the propagating wave front.

In some embodiments, the customizable lens may be designed using the iterative angular spectrum approach (IASA). In some embodiments, an algorithm implements IASA numerically by iteratively comparing simulated conditions at the target focal surface against the target conditions at the focal surface. In some embodiments, an algorithm implements IASA numerically by iteratively comparing simulated conditions at the focal surface against the target conditions at the focal surface; and the complex pressure distribution at the source to the results from the previous iterative step.

In a first step, the algorithm introduces lens geometry, propagating wave front, and target focal surface in a given medium. The target focal surface may be defined by its pressure pattern (p), made up of an amplitude map (A) and a phase map (Φ). The target focal surface is located some known distance from the lens.

The pressure wave equation includes amplitude and phase functions describing pressure at a given position in Euclidean space:

$$p(x,y,z) = \hat{p}(x,y,z) e^{j\Delta\Phi(x,y,z)} \quad (1)$$

where $\hat{p}(x, y, z)$ and $\Delta\Phi(x, y, z)$ are the amplitude and phase functions, respectively.

The IASA method uses fast Fourier transform (FFT) and inverse fast Fourier transform (IFFT) methods to converge to an optimum error criterion, calculated as an error between the target focal surface and conditions at the focal surface. The general form of the FFT equation in Euclidean space is shown in Equation 2:

$$P(k_x, k_y) = \int\int_{-\infty}^{+\infty} p(x, y, 0) e^{-j(k_x x + k_y y)} dx dy \quad (2)$$

The output of the FFT equation, P(kx,ky), gives an angular spectrum, where ki is the wavenumber in i space. The IFFT equation, excluding the evanescent wave components, is shown in Equation 3:

$$p(x, y, z) = \frac{1}{4\pi^2} \int\int_{k_x^2+k_y^2 \le k^2} P(k_x,k_y) e^{j\left(k_x x + k_y y + \sqrt{k^2 - k_x^2 - k_y^2} z\right)} dk_x dk_y \quad (3)$$

which provides the conditions at the focal surface in Euclidean space from the angular spectrum (P).

Figure 5:
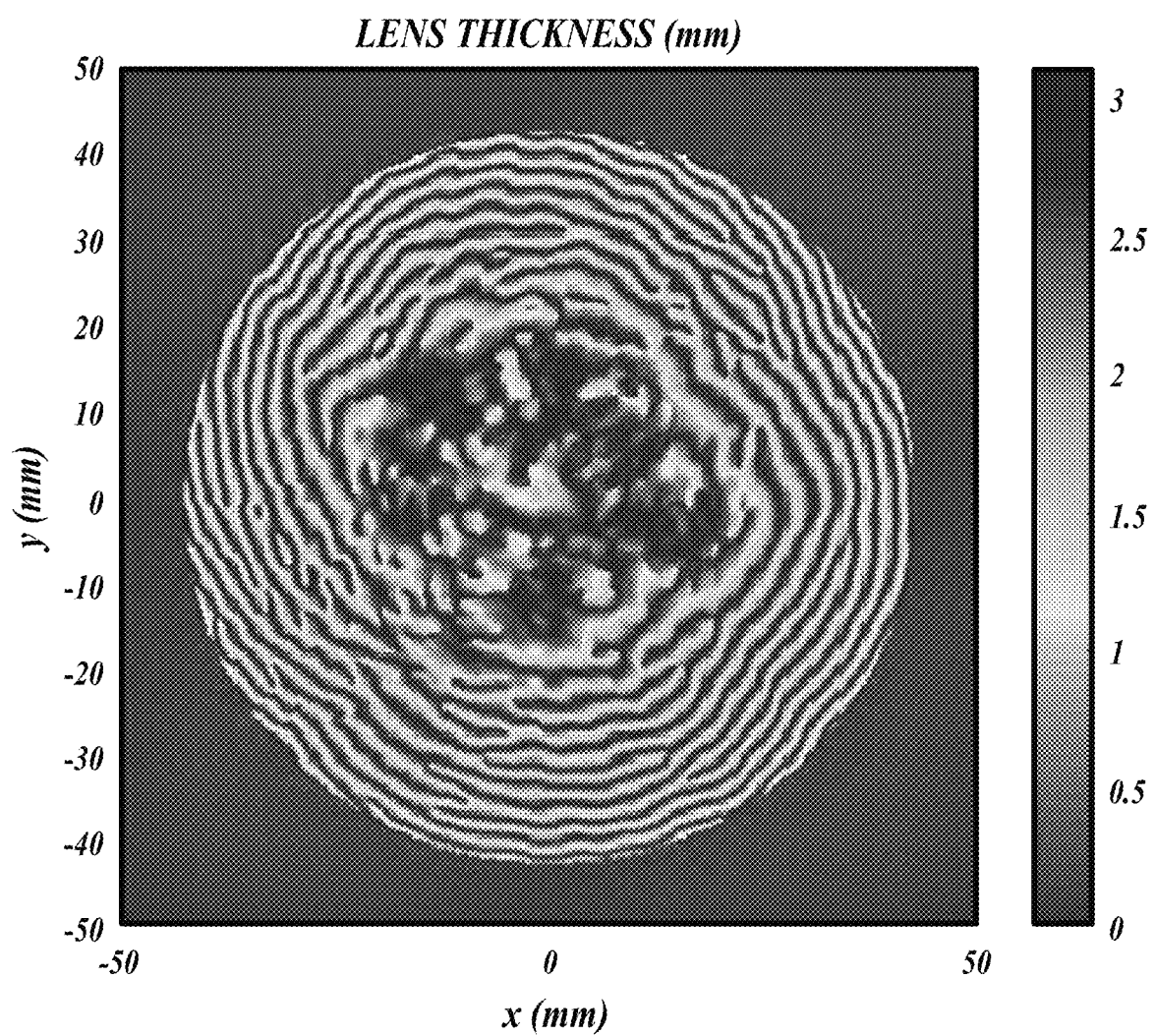
FIG. 5 is a graph of thickness of a holographic lens in accordance with an embodiment of the present technology.

In the initial iteration of the loop shown in FIG. 5, the propagating wave front is transformed by FFT into an angular spectrum. A propagation function, shown in Equation 4, then calculates the effect of movement through a given medium on the angular spectrum:

$$P(k_x, k_y, z) = P(k_x, k_y, 0) e^{jz\sqrt{k^2 - k_x^2 - k_y^2}} \quad (4)$$

which is used to calculate both propagation and back-propagation through the given medium between the focal surface and the lens. The propagating wave front then propagates through the lens and the given medium to produce an angular spectrum for a propagated wave front at the focal surface (the conditions at the focal surface).

As shown in FIG. 4, IFFT provides a wave equation in spatial coordinates for comparison to the desired conditions at the target focal surface. The error criterion indicates whether the lens design at the current iteration produces the target focal surface. In initial iterations, the error between the conditions at the focal surface and the target focal surface may be significant, due to near field effects that impact the propagating wave front.

To account for the near field effects, the IASA incorporates a back-propagation of the propagated wave front from the focal surface to the lens, shown as a clockwise lower arrow in FIG. 5, and modulates the propagating wave front, and its angular spectrum, for iterative propagation forward to the focal surface. The algorithm retains the latest iteration of the phase information at the focal surface to calculate convergence.

In addition to conventional IASA method, the method uses the multiple checks in the convergence criterion to meet our desired goals. The algorithm iteratively compares the convergence of the simulated conditions to the target image specified at each target location. Second, after the first iteration step and in parallel to the previous check, the algorithm compares the complex pressure distribution at the source to that of the previous step as well to speed up and improve the convergence calculation criterion. The comparisons in the previous two checks are specified to be within a specific error tolerance below which convergence to the optimal hologram solution is achieved. Finally, a maximum number of iterations is determined for each run, such that when it is exceeded the method terminates and saves the optimal hologram solution. The error tolerance and maximum number of iterations is determined based on the complexity of the hologram, such as, the number of target locations for phase and or amplitude at different frequencies. These checks of convergence are checked at each iteration step to yield the optimal solution.

Incorporating back propagation into an iterated forward propagating wave equation permits a more precise calculation of the conditions at the focal surface for subsequent adjustment of the lens geometry. With each cycle of forward propagation and back propagation the conditions at the focal surface and the conditions at the lens converge to an optimal solution.

An output of the IASA algorithm is the lens geometry. As described in Equation 5, a spatial thickness parameter describes the lens geometry by taking into account the transmission coefficient (a) of the system, including acoustic impedances (Z) of the lens material (h), the given medium (m), and a transducer (t), a source of acoustic waves:

$$a_T(x, y) = \frac{4 Z_t Z_h^2 Z_m}{z_h^2 (Z_t + Z_m)^2 \cos(k_h T(x, y))^2 + (Z_h^2 + Z_t Z_m)^2 \sin(k_h T(x, y))^2} \quad (5)$$

The thickness of the lens (T) can be calculated from the angular spectrum of the converged solution by creating a phase map for the surface of the lens. The lens creates constructive and destructive interference in the near-field by introducing phase offsets (ΔΦ) in the propagating wave front as it passes through the holographic lens. The thickness of the lens is described as follows in Equations 6-7:

$$\Delta\Phi(x,y) = (k_m - k_h)\Delta T(x,y) \quad (6)$$

where $$T(x,y) = T_0 - \Delta T(x,y). \quad (7)$$

The IASA algorithm is capable of designing a lens that produces multiple target focal surfaces at as many distances from the lens in a given medium. To accomplish this, the IASA algorithm separately incorporates the backpropagation from the wave equations of each of the target focal surfaces when modulating the propagating wave equation.

The IASA method can be used with different transducer geometries. For instance, for a focused transducer, the exact pressure field can be simulated and verified through holographic scanning in a plane. Next, the pressure field at the transducer aperture (obtained by back-projection) is used as the initial boundary condition over which we can impose the required phase to obtain the desired beam shape.

When compared to the conventional lens design methods, the IASA-based design method maximizes the power of the beam while producing an arbitrary pressure distribution in the plane of interest. Furthermore, the method can be extended to constrain the amplitude distribution in several different planes of propagation. Analogously, the method can be extended to produce different beam patterns using ultrasonic transducers at different frequencies. The method can also be used to constrain the phase distribution in one or more planes, or both amplitude and phase distributions simultaneously. The desired target field may be binary or continuously varying in amplitude and/or phase over the focal plane of interest.

FIG. 5 is a graph of thickness of a holographic lens in accordance with an embodiment of the present technology. In some embodiments, the holographic features of the illustrated lens may be obtained by the method described in conjunction with FIG. 4 above. For the illustrated flat holographic lens, the overall thickness of the lens changes with the height T of the particular holographic features.

Figure 6A:
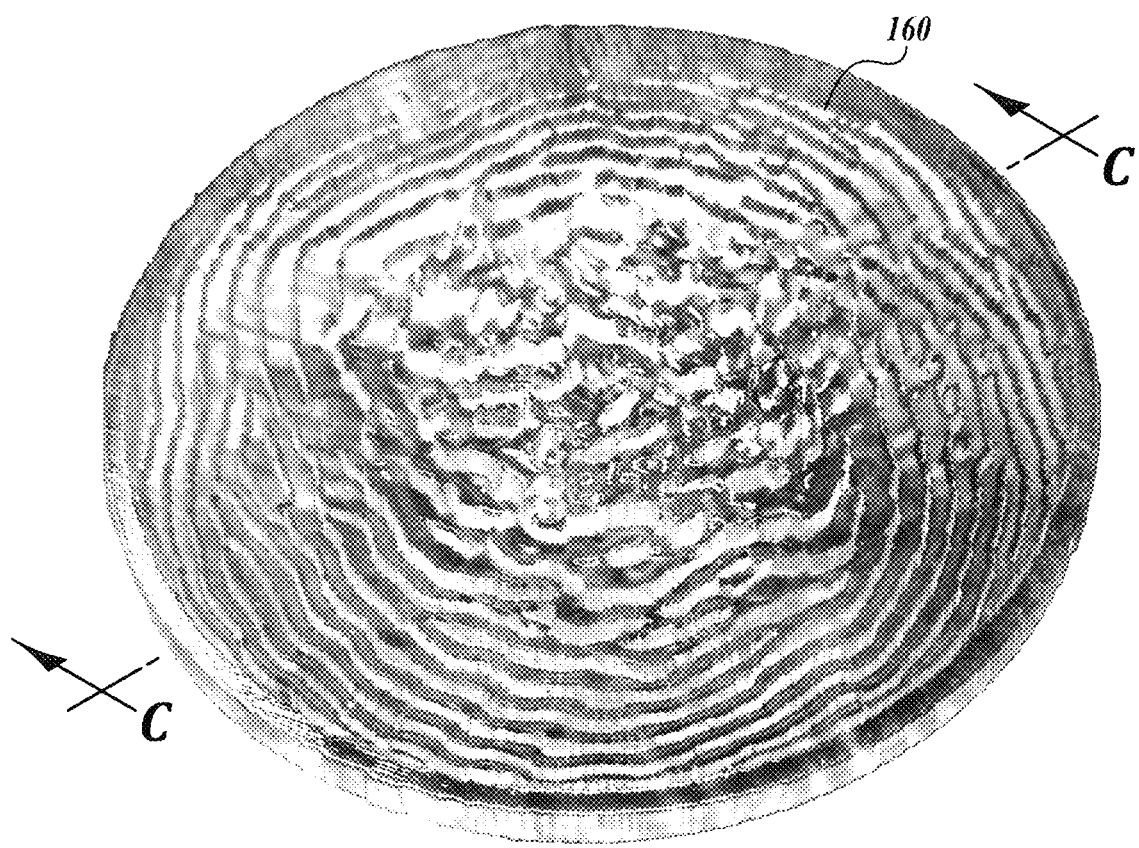
FIG. 6A is an isometric view of the lens in accordance with conventional technology.
Figure 6B:
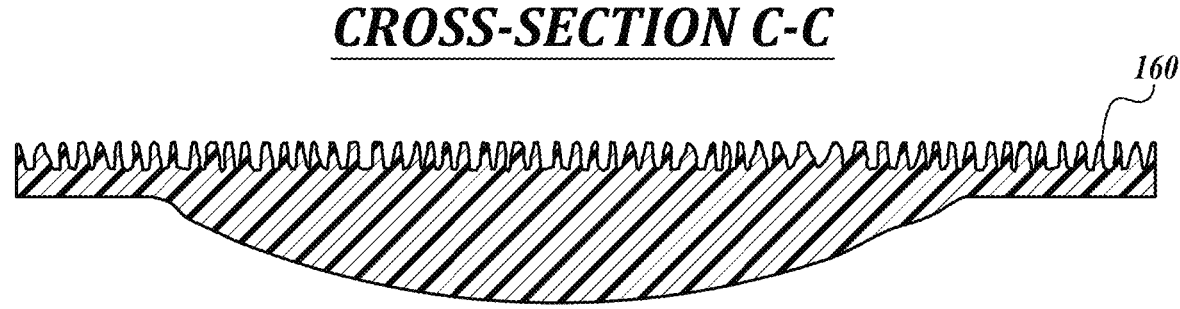
FIG. 6B is a cross-sectional view of the lens of FIG. 6A.

FIG. 6A is an isometric view of a holographic lens in accordance with conventional technology. FIG. 6B is a cross-sectional view of the lens of FIG. 6A.

In operation, a flat holographic lens may mate with a transducer having a flat outer surface. However, when mated to a transducer having a concave surface, the back surface of the holographic lens 160 must be shaped against the curved surface of transducer by adding material to the back side of the holographic lens. An example of such additional material that makes the holographic lens thicker is shown in the cross-sectional view of FIG. 6B.

Figure 7:
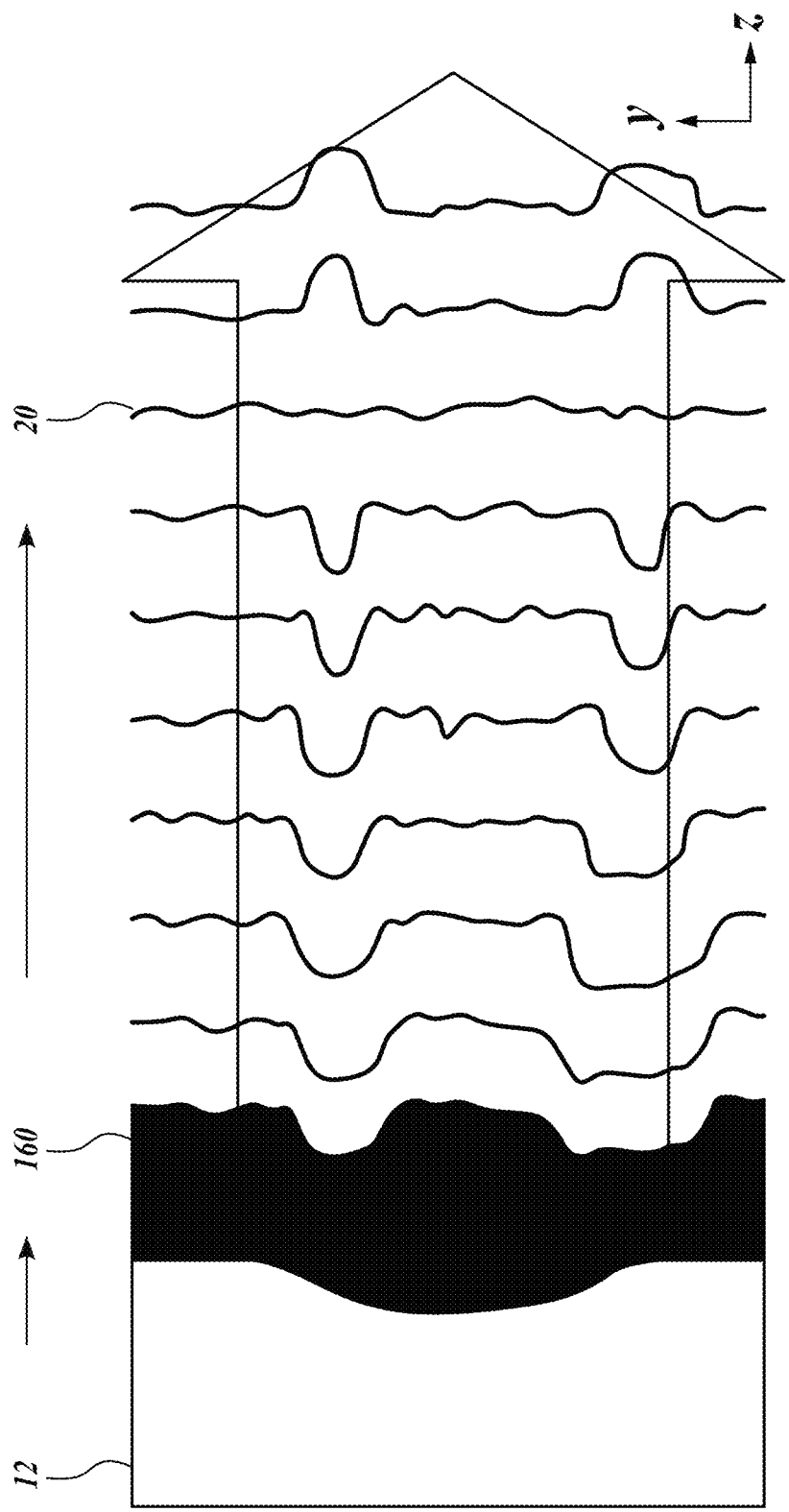
FIG. 7 is a schematic view of pressure waves produced by a lens in accordance with conventional technology.

FIG. 7 is a schematic view of pressure waves produced by the lens in accordance with conventional technology. When mated with a transducer that operates at the design frequency of the ultrasound, the holographic lens 160 generates illustrated ultrasound waves that are focused on an image plane (focal plane) 20. As explained above, the additional lens thickness increases energy dissipation and reduces the targeting precision of the lens.

Figure 8:
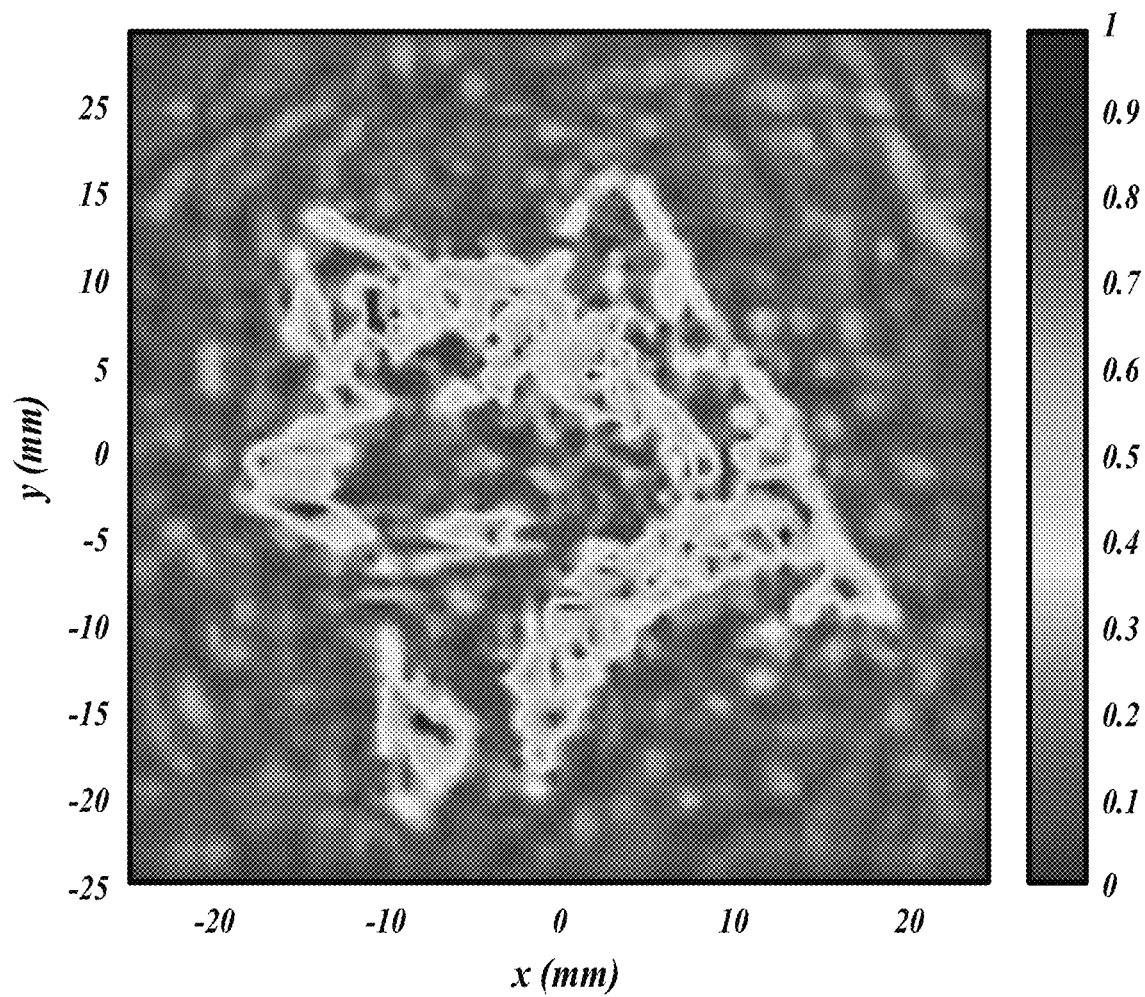
FIG. 8 is a graph of pressure amplitude for a sample target shown in FIG. 3 in accordance with conventional technology.

FIG. 8 is a graph of pressure amplitude for a sample target shown in FIG. 3. When the customizable lens is attached to the ultrasonic transducer to follow oscillations by the transducer, the local phases of the ultrasound at the surface of the customizable lens are offset due to the uneven thickness of the holographic lens. These phase offsets constructively/destructively combine to generate a pressure field at the target focal distance. In the illustrated embodiment, the pressure amplitude field attempts to emulate the target image shown in FIG. 3 at a prescribed distance from the source (i.e., at a prescribed distance from the transducer). In some applications, because of a relatively complex shape of the target, obtained pressure field may lack spatial resolution and the pressure amplitudes may be off the target values. In many cases, these shortcomings of the ultrasound pressure field at the target plane may be attributed to the additional thickness of the holographic lens, as explained above.

Figure 9:
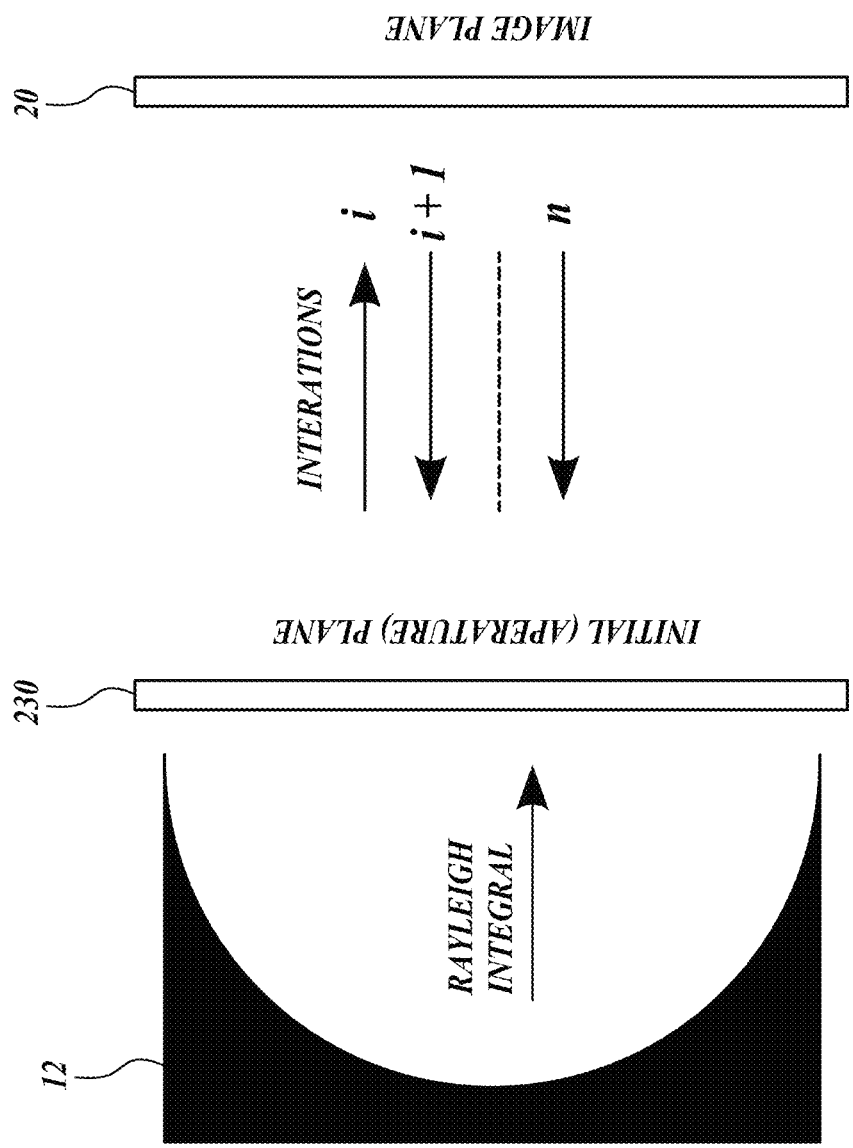
FIG. 9 is a schematic diagram of a method for designing a customizable lens in accordance with an embodiment of the present technology.

FIG. 9 is a schematic diagram of a method for designing a customizable lens 230 in accordance with an embodiment of the present technology. The method of designing may be understood as a two-step process. In the first step, an IASA algorithm as discussed with, for example, equations (1)-(7) may be used to design a flat holographic lens 230 based on the target pressure, phase, amplitude or velocity distribution of the ultrasound at the image plane 20. In the context of this disclosure, such flat holographic lens may be referred to as an intermediate customizable holographic lens characterized by the intermediate pressure/velocity plane that is a flat, two-dimensional surface.

In the second step, a Rayleigh integral method is used to determine the required holographic features of the curved holographic lens 230. The resulting curved holographic lens (non-planar holographic lens) 230 is characterized by the curvature of its principal plane in addition to the size and distribution of the holographic features, which in general differ from the holographic features of the corresponding flat holographic lens. In the context of this specification, the term principal plane of the holographic lens refers to the plane that approximately follows a middle of the thickness of the lens. In many practical applications of the inventive technology, the principal plane of the holographic lens 230 conforms to the curvature of the front surface (also referred to as the outer surface) of the transducer 12.

For a non-planar source like the illustrated front surface of the transducer 12, the Raileigh integral may be determined based on the boundary conditions of a focused source and complex pressure at aperture plane plus half wavelength (½λ) of the ultrasound being used. The Rayleigh integral to aperture plane may be expressed as:

$$P = \frac{-ik\rho c}{2\pi} \int\int V \frac{e^{ikR}}{R} dS \qquad (8)$$

assuming that the radius of curvature (R) of the front surface of the transducer is much higher than the ultrasound wavelength (R>>λ), which is a reasonable assumption for most practical ultrasonic transducers. The ultrasonic transducer 12 is illustrated as a single element transducer. In some embodiments, a frequency of the ultrasonic transducer is within a range from 100 kHz to 20 MHz. In some embodiments, a focal number of the customizable holographic lens is greater than 0.6. In some embodiments, a ratio of an aperture of the customizable holographic lens and a wavelength of the ultrasound greater than 20.

In the process of solving the Rayleigh integral, the holographic features are determined for the curved holographic lens. In general, the holographic features of the curved holographic lens are different from those of the flat holographic lens. Stated differently, it should not be assumed that the holographic features of the curved lens can be determined by simply bending a flat holographic lens into a mating position with a surface of the transducer. A person of ordinary skill would understand that such approach would result in erroneous summation/subtraction of the phases and amplitudes at the target focal plane. Determination of the holographic features of the curved holographic lens 230 is described in conjunction with FIGS. 10-11B below.

Figure 10:
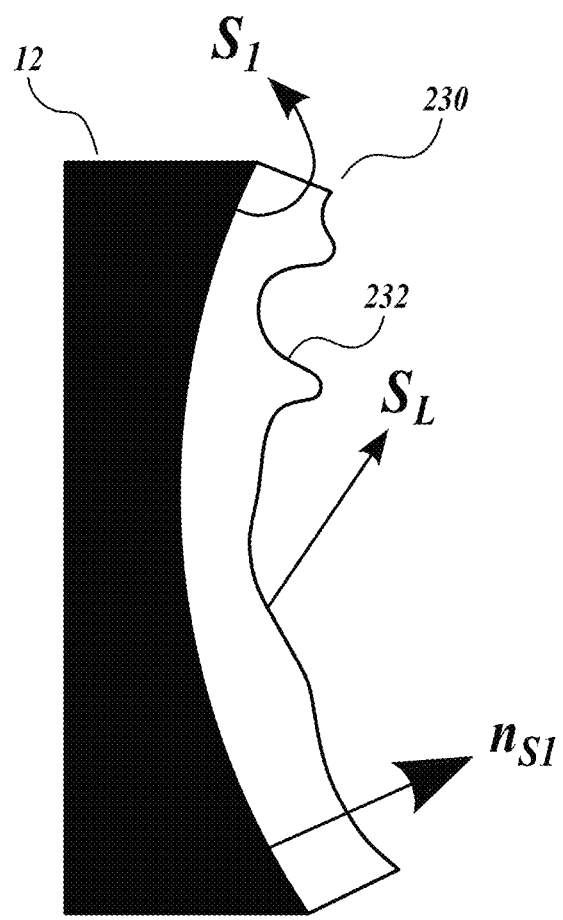
FIG. 10 is a schematic diagram of determining holographic features of the lens in accordance with an embodiment of the present technology.
Figure 11A:
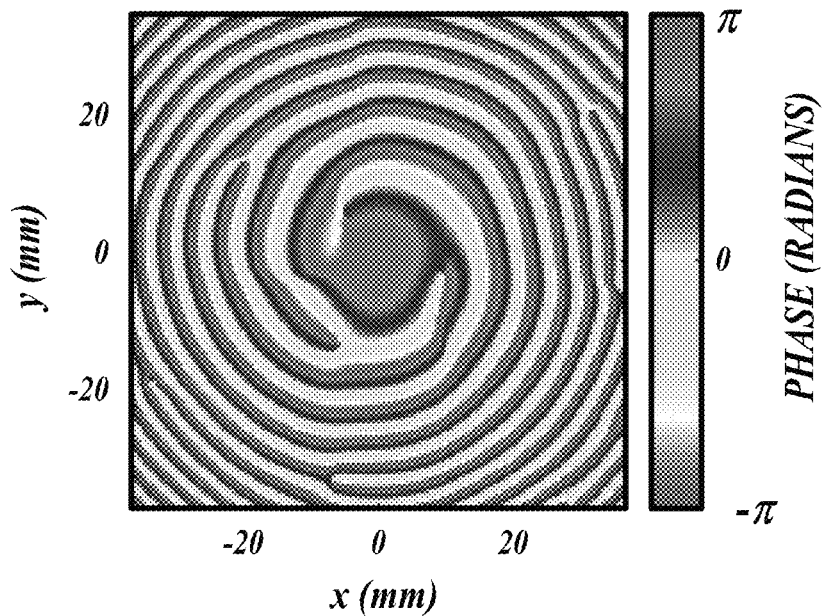
FIG. 11A is a phase solution at aperture plane a graph of a target phase boundary condition in accordance with an embodiment of the present technology.
Figure 11B:
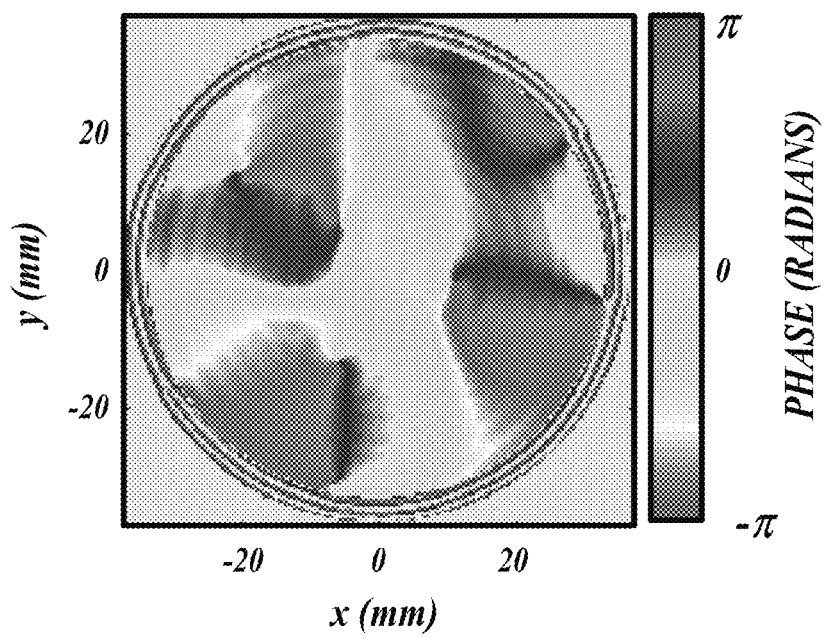
FIG. 11B illustrates a phase solution on a transducer surface in accordance with an embodiment of the present technology.

FIG. 10 is a schematic diagram of determining holographic features of the lens in accordance with an embodiment of the present technology. In some embodiments, a focused phase solution at the aperture plane (FIG. 11A) is backpropagated to the phase solution on curved surface of the transducer 12 (FIG. 11B) as:

$$\frac{\partial}{\partial n_{s1}} P_{S1} = \frac{1}{2\pi} \int\int P_{S2} \frac{\partial}{\partial n_{s1}} \frac{\partial}{\partial n_{s2}} \left(\frac{e^{ikR}}{R}\right) dS_2 \qquad (9)$$

where $n_{si}$ is $S_i$ surface normal. The resulting thickness (T) of the holographic lens 230 may be expressed as:

$$T = \frac{\phi}{k_0 - k_{lens}} \qquad (10)$$

where $k=2\pi/\lambda_i$, and $\lambda_i$ is wavelength in material i.

The lens surface $S_L$ of the curved holographic lens now becomes:

$$S_L - S_1 = (T+To) \cdot n_{S1} \qquad (11)$$

where T is the height of the holographic feature, and To is a constant thickness that adds no phase change.

In operation, the small-scale features (holographic features) 232 on the surface of the lens determine the phase offsets of the emitted ultrasound. When the ultrasound is generated at the required ultrasound frequency, these phase offsets constructively/destructively combine into a target pressure, velocity, amplitude and/or phase field.

A monolithic lens is described with reference to FIG. 10. However, in different embodiments, the lens 230 may also be a multi-element lens that comprises multiple segments.

The holographic lens 230 may be designed based on the target pressure amplitude/phase distributions, for example, as shown in FIG. 3. It is possible to obtain different distributions of different parameters (e.g., pressure, velocity, amplitude and phase) at different target distances from the source of ultrasound. As explained above, the size and distribution of the holographic features 232 of the curved holographic lens 230 is determined using the method outlined by the equations (1)-(11).

In some embodiments, a time-varying signal alters the beam pattern of a single-lensed transducer. For example, a curved holographic lens 230 may generate multiple patterns at different frequencies simultaneously, or may generate a single pressure pattern for a finite temporal period. In an embodiment, the frequency of a sinusoidal ultrasound signal may be varied over time to change the pattern, either continuously as a frequency chirp, or discretely in intervals. In another embodiment, a short signal pulse may be generated by the transducer to produce a temporary holographic image for a therapy such as shock wave lithotripsy, burst wave lithotripsy, or histotripsy. In other embodiments, the customizable lens may be designed to produce a target distribution of ultrasound phases that, for example, pushes the target in a desired direction. In some embodiments, the inventive technology is used for diagnostic imaging, image guidance, or microbubble manipulation.

Figure 12:
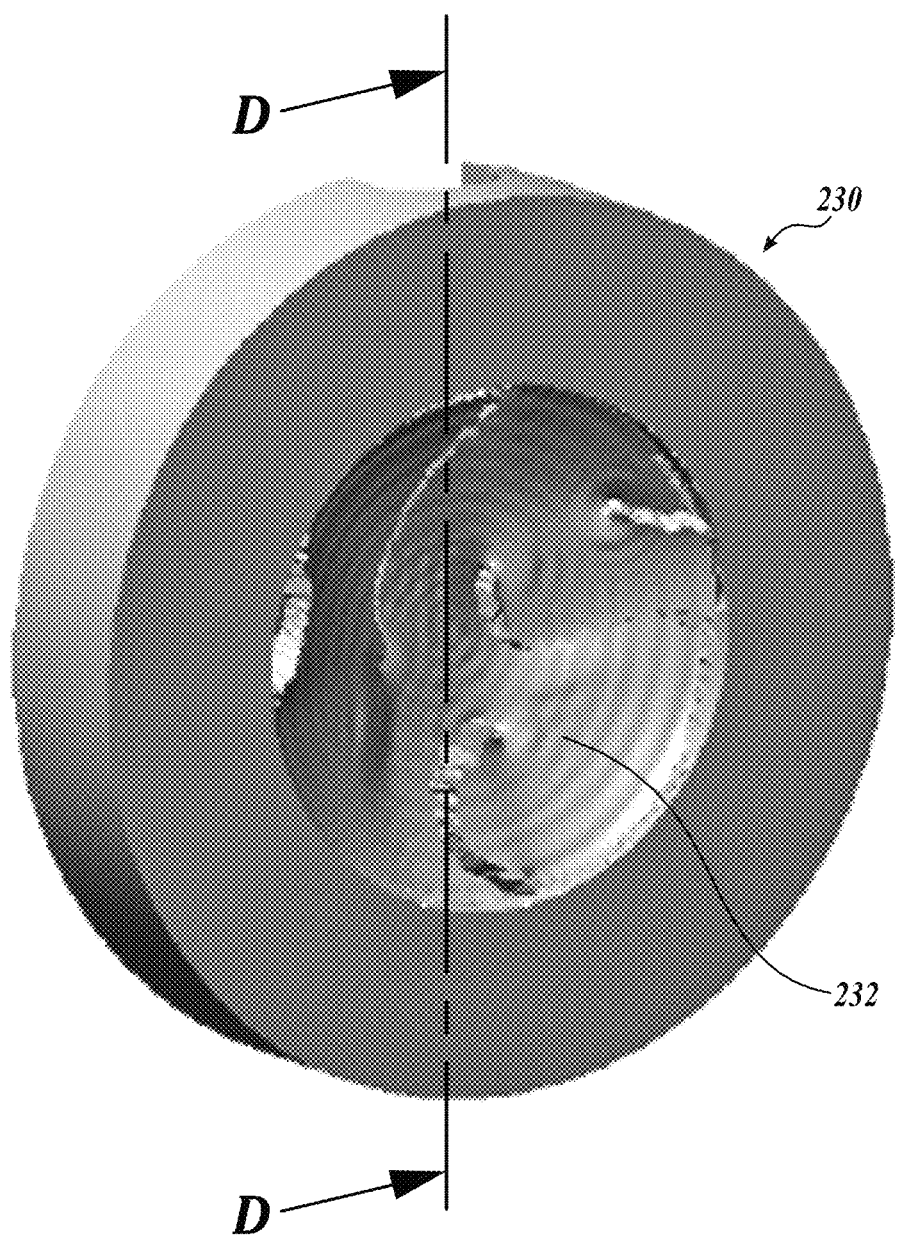
FIG. 12 is an isometric view of a curved holographic lens in accordance with an embodiment of the present technology.

FIG. 12 is an isometric view of a curved holographic lens 230 in accordance with an embodiment of the present technology. The holographic lens 230 is illustrated as facing the object to be treated, i.e., the holographic features 232 face the object to be treated.

In some embodiments, the customizable lens 230 is made by machining or by additive manufacturing processes, for example, by 3D printing. In other embodiments, the customizable lens may be made by machining or injection molding. The customizable lens 230 may be manufactured from glass, graphite, metal, epoxy, composite with suitable acoustic properties or plastic that has suitable transmission coefficients for the ultrasound frequency. In some embodiments, the customizable lens 230 may have a curvature to achieve focusing or defocusing simultaneously with image formation (e.g., formation of the target pressure field or phase distribution). The lens resolution is generally determined by the method of manufacture, but in some applications the lens resolution can be smaller than a wavelength. Plane D-D indicates a cross-sectional plane of the holographic lens 230.

Figure 12A:
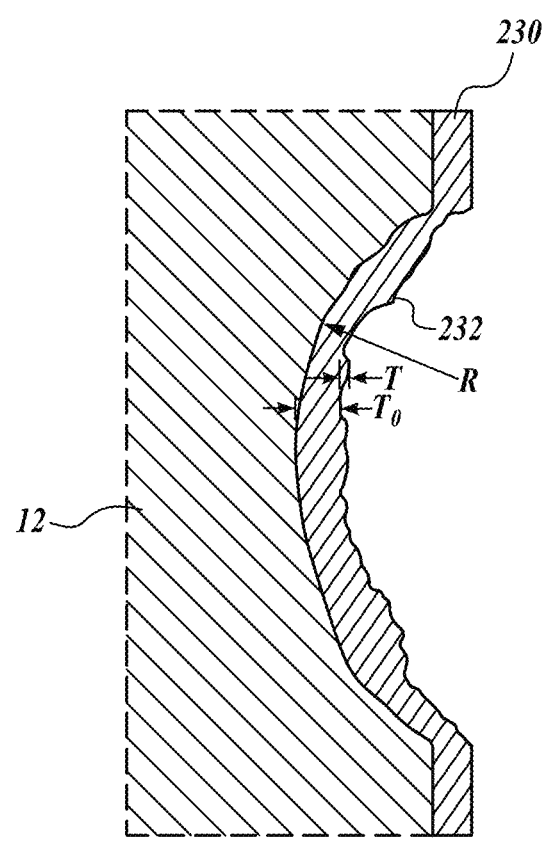
FIG. 12A is a cross sectional view of a curved holographic lens in accordance with an embodiment of the present technology.

FIG. 12A is a cross sectional view D-D of the curved holographic lens of FIG. 12. The holographic lens 230 is designed such that the back side of the lens follows the curvature R of the transducer 12. In some embodiments, an interface 14 (not shown) is disposed between the transducer and holographic lens. The holographic lens 230 has a generally uniform thickness To, save for the differing heights T of the individual holographic features 232. As a result, the targeting accuracy and pressure amplitude/phase distribution are improved in comparison to the holographic lenses having non-uniform thickness, for example, the holographic lens illustrated in FIG. 6B.

Figure 13:
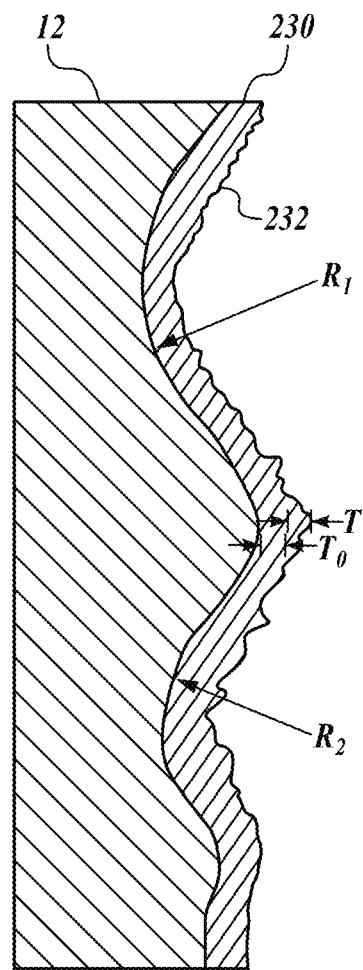
FIG. 13 is a cross-sectional view of a curved holographic lens in accordance with an embodiment of the present technology.

FIG. 13 is a cross-sectional view of a curved holographic lens in accordance with an embodiment of the present technology. In some embodiments, the transducer 12 may be characterized by a wavy surface to which the curved holographic lens 230 mates. In the illustrated example, the transducer's surface is characterized by different radii R1 and R2, but in other embodiments, radii R1 and R2 may be same. In other embodiments, the transducer's surface may be characterized by more than two radii, that is, by more than two different curvatures. In some embodiments, a curvature of the front surface of the ultrasonic transducer is a spherical, parabolic or elliptical curvature. In some embodiments, a curvature of the front surface of the ultrasonic transducer is a non-constant curvature disposed along multiple directions.

Figure 14A:
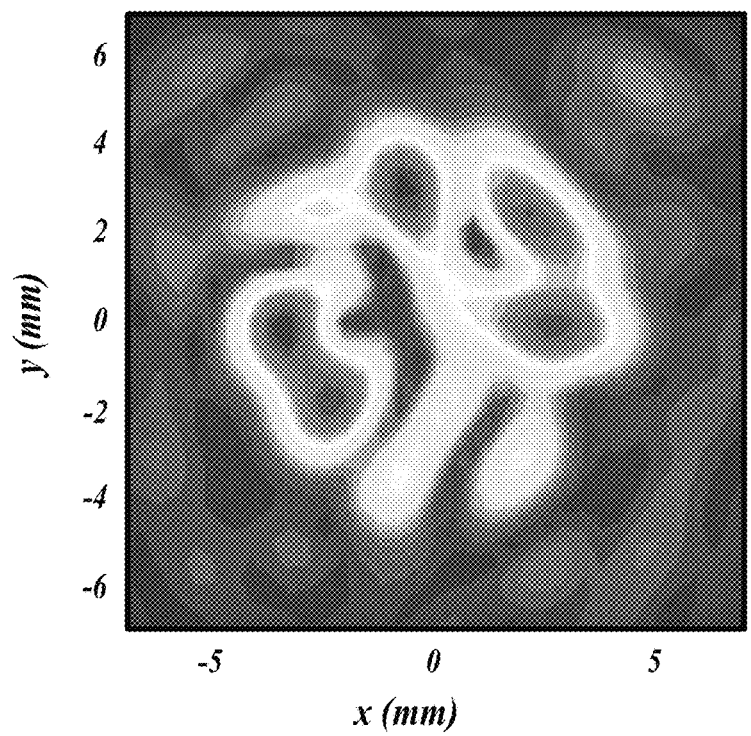
FIGS. 14A and 14B are graphs of simulated and measured pressure amplitude, respectively, at a target image plane of ultrasound in accordance with an embodiment of the present technology.
Figure 14B:
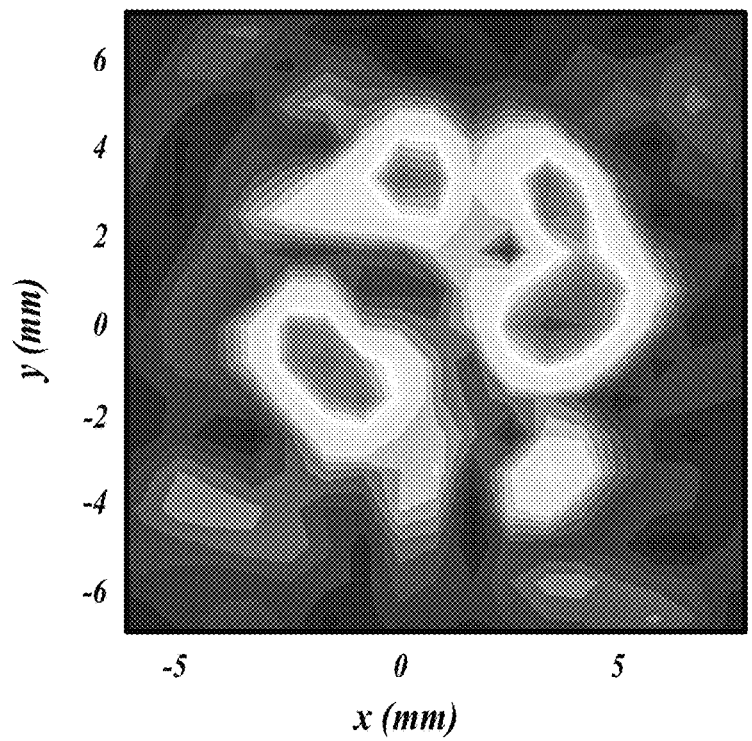

FIGS. 14A and 14B are graphs of simulated and measured pressure amplitude, respectively, achieved by a curved holographic lens at a target image plane of ultrasound in accordance with an embodiment of the present technology. The horizontal and vertical axes indicate the size of the image plane in mm Pressures are normalized for comparisons. The measured field of FIG. 14B is obtained by holography field propagation, i.e., a holography scan is used to propagate the pressure field in 3D. An excellent agreement is achieved between the simulated pressure amplitude (FIG. 14A) and measured pressure amplitude (FIG. 14B). Deviation was quantified using relative change in Frobenius norm. A difference between the simulated and measured fields can be expressed (in percentage) as:

$$\delta = \frac{<P(x, y)_{sim.}, P(x, y)_{sim.}> - <P(x, y)_{meas.}, P(x, y)_{meas.}>}{<P(x, y)_{sim.}, P(x, y)_{sim.}>} \times 100 \quad (12)$$

For the illustrated pressure amplitude fields in FIGS. 14A and 14B, the value of $\delta$ corresponds to 4.8%. This is considered a very good result, which far exceeds the performance of a flat holographic lens under the same conditions. Analogously, a difference $\delta$ between the pressure amplitude for a curved holographic lens in the xz-plane corresponds to about $\delta=16\%$, which, again, far exceeds the performance of a flat holographic lens under the same conditions.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

What is claimed is:

1. An ultrasonic therapy system configured to apply ultrasound to a target in a body, comprising:
   an ultrasonic transducer configured to generate the ultrasound; and
   a curved holographic lens configured to focus the ultrasound onto a focal area of the target that is an object or a portion of the object in the body, wherein the curved holographic lens comprises holographic features that are based on the target and based on a known curved shape of the transducer that is different than its flat projection, and wherein, as designed, the curved holographic lens is curved to directly mate with a curved front surface of the ultrasonic transducer, wherein the holographic features of the curved holographic lens are determined by:

a first step of applying an iterative angular spectrum approach (IASA) algorithm to design a flat holographic lens;

a second step of applying a Rayleigh integral method to determine the holographic features of the curved holographic lens based on acoustic boundary conditions at the curved front surface of the ultrasonic transducer; and a third step of determining thickness and direction of the holographic features of the curved holographic lens by defining a lens surface SL of the curved holographic lens as:

$$S_L - S_1 = (T + To) \cdot n_{s1}$$

where T is a height of a holographic feature of the flat holographic lens that is expressed as:

$$T = \Phi / k_o - k_{lens}$$

where $\Phi$ is a phase on the curved front surface of the ultrasonic transducer, $k = 2\pi / \lambda_i$, $\lambda_i$ is wavelength in material i, $n_{si}$ is $S_i$ surface normal, To is a constant thickness of the curved holographic lens that adds no phase change, S1 is a backside of the curved holographic lens that matches the front surface of the ultrasonic transducer, and $S_L$ is a frontside of the curved holographic lens defining holographic features of the curved holographic lens.

2. The system of claim 1, wherein the target is defined by at least one acquired image of the object in the body.

3. The system of claim 1, wherein a curvature of the front surface of the ultrasonic transducer is a spherical, parabolic or elliptical curvature.

4. The system of claim 1, wherein the front surface of the ultrasonic transducer comprises more than one curvature.

5. The system of claim 1, wherein a curvature of the front surface of the ultrasonic transducer is a non-constant curvature disposed along multiple directions.

6. The system of claim 1, wherein the curved holographic lens is a three-dimensional (3D) printed lens.

7. The system of claim 1, wherein the curved holographic lens is produced by machining or injection molding.

8. The system of claim 1, wherein the ultrasound is configured to produce at least one of a thermal therapy, a histotripsy, a lithotripsy, a drug delivery, a diagnostic imaging, an image guidance, a microbubble manipulation, and a manipulation and removal of urinary stone fragments at the target.

* * * * *